United States Patent [19]

Guaciaro

[11] Patent Number: 5,354,727

[45] Date of Patent: Oct. 11, 1994

[54] 2-(1-SUBSTITUTED-2-IMIDAZOLIN-2-YL)BENZOIC AND NICOTINIC ACIDS AND A METHOD FOR THEIR PREPARATION

[75] Inventor: Michael A. Guaciaro, Hightstown, N.J.

[73] Assignee: American Cyanamid Company, Wayne, N.J.

[21] Appl. No.: 9,160

[22] Filed: Jan. 26, 1993

Related U.S. Application Data

[62] Division of Ser. No. 762,836, Sep. 19, 1991, Pat. No. 5,213,607, which is a division of Ser. No. 453,659, Dec. 20, 1989, Pat. No. 5,062,881.

[51] Int. Cl.$^5$ .................. A01N 43/50; A01N 57/16; C07D 233/20; C07D 233/32
[52] U.S. Cl. .................. 504/193; 504/197; 504/277; 548/110; 548/111; 548/300.7; 548/316.4; 548/316.7; 548/323.5; 548/324.1; 548/324.5; 548/325.5
[58] Field of Search .............. 504/277, 197, 193; 548/316.4, 316.7, 323.5, 324.1, 324.5, 325.5, 337.1, 341.1, 342.5, 343.1, 343.5

[56] References Cited

U.S. PATENT DOCUMENTS

| | | | |
|---|---|---|---|
| 4,188,487 | 2/1980 | Los | 548/325.5 |
| 4,314,844 | 2/1982 | Swithenbank et al. | 504/275 |
| 4,404,012 | 9/1983 | Orwick et al. | 504/253 |
| 4,614,535 | 9/1986 | Schmier et al. | 504/253 |
| 4,615,726 | 10/1986 | Schmier et al. | 504/225 |
| 4,740,233 | 4/1988 | Kleschick et al. | 504/214 |
| 4,798,619 | 1/1989 | Los | 504/156 |
| 4,911,753 | 3/1990 | Los | 504/156 |

Primary Examiner—Richard L. Raymond
Assistant Examiner—Brian Bembenick
Attorney, Agent, or Firm—John W. Hogan, Jr.

[57] ABSTRACT

2-(1-Substituted-2-imidazolin-2-yl)benzoic and nicotinic acids, and derivatives thereof, which are effective in the control of undesirable plant species are described, Also described are a method for the herbicidal use of the compounds and a method for their preparation.

5 Claims, No Drawings

2-(1-SUBSTITUTED-2-IMIDAZOLIN-2-YL)BENZOIC AND NICOTINIC ACIDS AND A METHOD FOR THEIR PREPARATION

This is a divisional of co-pending application Ser. No. 07/762,836 filed on Sep. 19, 1991 (now U.S. Pat. No. 5,213,607) which is a divisional of Ser. No. 07/453,659 filed on Dec. 20, 1989, now U.S. Pat. No. 5,062,881.

BACKGROUND OF THE INVENTION

Arylimidazolinones are a class of potent herbicides useful in the control of a wide variety of undesirable plant species. Pyridyl- and quinolyl-imidazolinones and their use is disclosed in Los U.S. Pat. No. 4,798,619 and imidazolinyl benzoic acids and their use is disclosed in Los U.S. Pat. No. 4,188,487.

The present invention describes 2-(1-substituted-2-imidazolin-2-yl)benzoic and nicotinic acids, and derivatives thereof, which differ from U.S. Pat. No. 4,798,619 and U.S. Pat. No. 4,188,487 according to the substitution of the I position on the imidazolinone ring. Methods to attach a hydroxyl group directly to the nitrogen atom of the imidazolinone ring system are not known in the art. Likewise, the attachment of a nitrile or an arylthio moiety to a nitrogen atom in the imidazolinone ring system has heretofore never been disclosed in the art. No known methods are indicated for adding electrophilic functional groups to an imidazolinone nitrogen.

It is an object of the present invention to provide 2-(1-substituted-2-imidazolin-2-yl)benzoic and nicotinic acids, and derivatives thereof that demonstrate broadened crop selectivity and retention of weed control. This and other objects will become more apparent in the description of the invention.

SUMMARY OF THE INVENTION

The present invention describes 2-(1-substituted-2-imidazolin-2-yl)benzoic and nicotinic acids, and derivatives thereof, useful as herbicidal agents for a variety of crops and a method for their preparation.

The 2-(1-substituted-2-imidazolin-2-yl)benzoic and nicotinic acids, and derivatives thereof, of the present invention are illustrated as structural formula I:

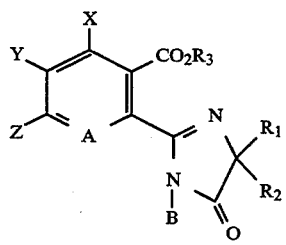

(I)

wherein
X is hydrogen, halogen or methyl;
Y and Z are each hydrogen, halogen, $C_1$–$C_6$ alkyl optionally substituted with $C_1$–$C_3$ alkoxy
$C_1$–$C_3$ alkoxy, phenoxy, $C_1$–$C_3$ haloalkyl, trifluoromethoxy, $C_1$–$C_4$ hydroxyalkyl, $C_1$–$C_4$ alkylthio, formyl, difluoromethoxy, 1,1,2,2-tetrafluoroethoxy, nitro, cyano, $C_1$–$C_4$ alkylsulfonyl, $C_2$–$C_6$ alkenyl optionally substituted with halogen;
$C_2$–$C_6$ alkynyl optionally substituted with halogen;
or phenyl optionally substituted with $C_1$–$C_3$ alkyl, $C_1$–$C_3$ alkoxy, or halogen;
and, when taken together, Y and Z may form a ring in which YZ are represented by the structure: —$(CH_2)_n$—, where n is an integer of 3 or 4; or

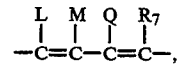

where L, M, Q and $R_7$ are each hydrogen, halogen, $C_1$–$C_4$ alkyl, $C_1$–$C_4$ alkoxy, $C_1$–$C_4$ alkylsulfonyl, $C_1$–$C_4$ haloalkyl, difluoromethoxy, trifluoromethoxy, 1,1,2,2-tetrafluoroethoxy, nitro, cyano, phenyl optionally substituted with halogen or $C_1$–$C_3$ alkyl;
phenoxy optionally substituted with halogen, trifluoromethyl, nitro or $C_1$–$C_3$ alkyl;
$C_3$–$C_6$ alkenyl optionally substituted with halogen;
or $C_3$–$C_6$ alkynyl optionally substituted with halogen;
A is $CR_6$ or nitrogen;
B is hydroxyl, cyano, halogen, $SR_4$,

$R_1$ is $C_1$–$C_4$ alkyl;
$R_2$ is $C_1$–$C_4$ alkyl or $C_3$–$C_6$ cycloalkyl;
and when $R_1$ and $R_2$ are taken together with the carbon to which they are attached they may represent $C_3$–$C_6$ cycloalkyl optionally substituted with methyl;
$R_3$ is hydrogen,
$C_1$–$C_6$ alkyl optionally substituted with $C_1$–$C_3$ alkoxy, halogen, $C_3$–$C_6$ cycloalkyl, benzyl, furyl, trimethylsilyl, phenyl, halophenyl, $C_1$–$C_4$ alkylphenyl, $C_1$–$C_4$ alkoxyphenyl, or nitrophenyl;
$C_3$–$C_6$ alkenyl optionally substituted with $C_1$–$C_3$ alkoxy, phenyl, halogen or $C_1$–$C_4$ alkoxycarbonyl;
$C_3$–$C_6$ cycloalkyl optionally substituted with $C_1$–$C_3$ alkyl;
$C_3$–$C_6$ alkynyl optionally substituted with $C_1$–$C_3$ alkyl; or
a cation of alkali metals, ammonium or organic ammonium;
$R_4$ is $C_1$–$C_4$ alkyl, or phenyl optionally substituted with nitro, $CO_2R_8$, cyano, trifluoromethyl, difluoromethyl, $C_1$–$C_4$ alkyl, $C_1$–$C_4$ alkoxy, or halogen;
$R_5$ is $C_1$–$C_4$ alkyl;
$R_6$ is hydrogen, halogen, $C_1$–$C_4$ alkyl, $C_1$–$C_4$ alkoxy, trifluoromethyl, trifluoromethoxy, difluoromethoxy or 1,1,2-2-tetrafluoroethoxy;
$R_8$ is hydrogen or $C_1$–$C_4$ alkyl;
the N-oxides thereof, when $R_3$ is not unsaturated alkyl and Y and Z cannot be unsaturated alkyl or alkylthio;
the optical isomers thereof, when $R_1$ and $R_2$ represent different substituents; and
the acid addition salts thereof, when $R_3$ is other than a cation.

The compounds of the present invention demonstrate a broad spectrum of selectivity on important agronomic crops such as corn, wheat and soybeans while effectively controlling numerous weed species.

DETAILED DESCRIPTION OF THE INVENTION

The 2-(1-substituted-2-imidazolin-2-yl)benzoic and nicotinic acids, and derivatives thereof, of the present invention are useful in the control of a wide variety of undesirable plant species.

The 2-(1-substituted-2-imidazolin-2-yl)benzoic and nicotinic acids, and derivatives thereof, of the present invention are represented by formula I:

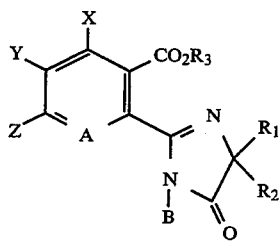

(I)

wherein

X is hydrogen, halogen or methyl;

Y and Z are each hydrogen, halogen,
  $C_1$–$C_6$ alkyl optionally substituted with $C_1$–$C_3$ alkoxy;
  $C_1$–$C_3$ alkoxy, phenoxy, $C_1$–$C_3$ haloalkyl, trifluoromethoxy, $C_1$–$C_4$ hydroxyalkyl, $C_1$–$C_4$ alkylthio, formyl, difluoromethoxy, 1,1,2,2-tetrafluoroethoxy, nitro, cyano, $C_1$–$C_4$ alkylsulfonyl, $C_2$–$C_6$ alkenyl optionally substituted with halogen;
  $C_2$–$C_6$ alkynyl optionally substituted with halogen;
  or phenyl optionally substituted with $C_1$–$C_3$ alkyl, $C_1$–$C_3$ alkoxy, or halogen;

and, when taken together, Y and Z may form a ring in which YZ are represented by the structure: $-(CH_2)_n-$, where n is an integer of 3 or 4; or

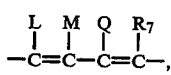

where L, M, Q and $R_7$ are each hydrogen, halogen, $C_1$–$C_4$ alkyl, $C_1$–$C_4$ alkoxy, $C_1$–$C_4$ alkylsulfonyl, $C_1$–$C_4$ haloalkyl, difluoromethoxy, trifluoromethoxy, 1,1,2,2-tetrafluoroethoxy, nitro, cyano, phenyl optionally substituted with halogen or $C_1$–$C_3$ alkyl;
phenoxy optionally substituted with halogen, trifluoromethyl, nitro or $C_1$–$C_3$ alkyl; $C_3$–$C_6$ alkenyl optionally substituted with halogen; or $C_3$–$C_6$ alkynyl optionally substituted with halogen;

A is $CR_6$ or nitrogen;

B is hydroxyl, cyano, halogen, $SR_4$,

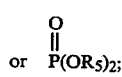

$R_1$ is $C_1$–$C_4$ alkyl;

$R_2$ is $C_1$–$C_4$ alkyl or $C_3$–$C_6$ cycloalkyl;

and when $R_1$ and $R_2$ are taken together with the carbon to which they are attached they may represent $C_3$–$C_6$ cycloalkyl optionally substituted with methyl;

$R_3$ is hydrogen,
  $C_1$–$C_6$ alkyl optionally substituted with $C_1$–$C_3$ alkoxy, halogen, $C_3$–$C_6$ cycloalkyl, benzyl, furyl, trimethylsilyl, phenyl, halophenyl, $C_1$–$C_4$ alkylphenyl, $C_1$–$C_4$ alkoxyphenyl, or nitrophenyl;
  $C_3$–$C_6$ alkenyl optionally substituted with $C_1$–$C_3$ alkoxy, phenyl, halogen or $C_1$–$C_4$ alkoxycarbonyl;
  $C_3$–$C_6$ cycloalkyl optionally substituted with $C_1$–$C_3$ alkyl;
  $C_3$–$C_6$ alkynyl optionally substituted with $C_1$–$C_3$ alkyl; or
  a cation of alkali metals, ammonium or organic ammonium;

$R_4$ is $C_1$–$C_4$ alkyl, or phenyl optionally substituted with nitro, $CO_2R_8$, cyano, trifluoromethyl, difluoromethyl, $C_1$–$C_4$ alkyl, $C_1$–$C_4$ alkoxy, or halogen;

$R_5$ is $C_1$–$C_4$ alkyl;

$R_6$ is hydrogen, halogen, $C_1$–$C_4$ alkyl, $C_1$–$C_4$ alkoxy, trifluoromethyl, trifluoromethoxy, difluoromethoxy or 1,1,2-2-tetrafluoroethoxy;

$R_8$ is hydrogen or $C_1$–$C_4$ alkyl;

the N-oxides thereof, when $R_3$ is not unsaturated alkyl and Y and Z cannot be unsaturated alkyl or alkylthio;

the optical isomers thereof, when $R_1$ and $R_2$ represent different substituents; and the acid addition salts thereof, when $R_3$ is other than a cation.

A preferred group of 2-(1-substituted-2-imidazolin-2-yl)benzoic and nicotinic acids, and derivatives thereof, that is especially effective in the control of undesirable plant species in agronomic crops is illustrated by formula

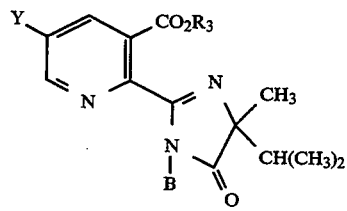

(II)

wherein

B, $R_4$, $R_5$ and $R_8$ are as described above;

Y is hydrogen, halogen, $C_1$–$C_4$ alkyl optionally substituted with $C_1$–$C_3$ alkoxy or $C_1$–$C_3$ alkoxy; and $R_3$ is hydrogen;
  $C_1$–$C_6$ alkyl optionally substituted with phenyl, halophenyl, $C_1$–$C_4$ alkylphenyl, $C_1$–$C_4$ alkoxyphenyl, or nitrophenyl;
  $C_3$–$C_6$ alkenyl;
  $C_3$–$C_6$ alkynyl; or
  a cation of alkali metals, ammonium or organic ammonium.

In formulas (I) and (II) above, alkali metals include: sodium, potassium and lithium, but sodium is generally preferred. Further, the term "organic ammonium" is defined as a group consisting of a positively charged nitrogen atom joined to from one to four aliphatic groups, each containing from one to sixteen carbon atoms.

Surprisingly the compounds of the present invention demonstrate a broadened spectrum of selectivity on important agronomic crops such as corn, wheat and soybeans while effectively controlling numerous weed species.

Certain formula I 2-(1-substituted-2-imidazolin-2-yl)benzoic and nicotinic acids, and derivatives thereof, may be formed by reacting a phthalaldehydate or a 2-formylnicotinate with at least an equivalent amount of hydroxylamine hydrochloride, in an aqueous alcohol solution, to yield the formula III first intermediate

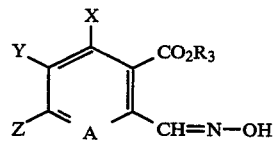

wherein X, Y, Z and A are as described for formula I; and $R_3$ is $C_1$–$C_5$ alkyl or benzyl. Reacting said first intermediate with at least an equivalent amount of a chlorinating agent such as chlorine, N-chlorosuccinimide or the like yields an o-(chloroformyl)benzoate, o-oxime or an o-(chloroformyl)nicotinate, o-oxime. Reacting said chloroformyl oxime with at least an equivalent amount of an aminocarboxylate and a base in an inert organic solvent yields the formula IV second intermediate:

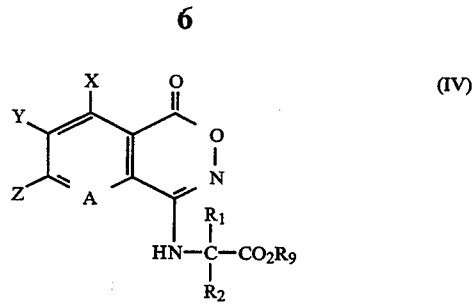

wherein X, Y, Z, A, $R_1$ and $R_2$ are as described for formula I; and $R_9$ is $C_1$–$C_4$ alkyl. Reacting said second intermediate with at least 2 equivalents of a base, in an organic solvent such as benzene, tetrahydrofuran, toluene, dioxane or the like, dissolving the resultant salt of 2-(1-hydroxy-5-oxo-2-imidazolin-2-yl)benzoic or nicotinic acid in water, adjusting the pH of the aqueous solution to 1.0–4.0 with a mineral acid yields the formula I 2-(1-hydroxy-5-oxo-2-imidazolin-2-yl)benzoic or nicotinic acid. Other formula I compounds may be prepared by reacting said benzoic or nicotinic acid with diazomethane to yield a 2-(1-substituted-2-imidazolin-2-yl)benzoate or nicotinate. This reaction scheme is illustrated in flow diagram I:

Flow Diagram I

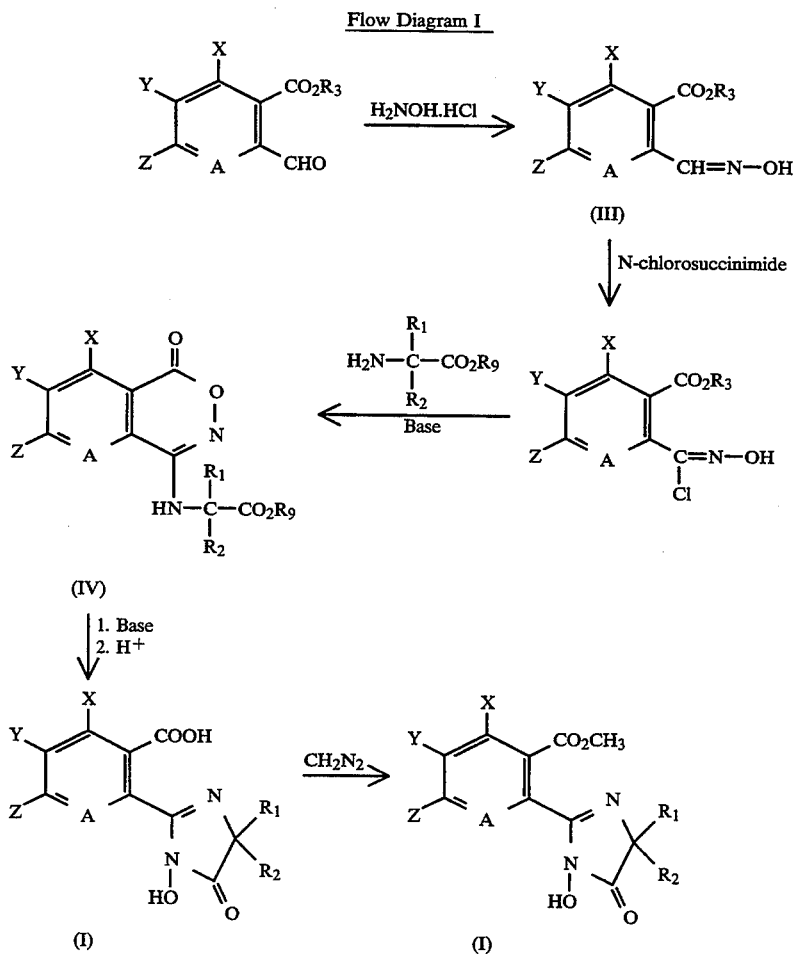

Preparation of formula I 2-(1-substituted-2-imidazolin-2-yl)benzoates and nicotinates can also be achieved by reaction of the appropriately substituted imidazolinyl nicotinate or benzoate wherein X, Y, Z, A, $R_1$, $R_2$ and $R_3$ are as described for formula I with the proviso that $R_3$ cannot be hydrogen or a cation and B is hydrogen, with the appropriate cyanogen halide, substituted phenylsulfinyl chloride, alkylsulfinyl chloride or dialkyl chlorophosphate, and a suitable base, for example, cyanogen bromide and sodium hydride. This reaction provides a 2-(1-substituted-2-imidazolin-2-yl)benzoate or nicotinate having the same substituents as the starting material, but in addition is substituted on the 1-position of the imidazolinone with cyano. In a similar reaction 2-nitrobenzenesulfinyl chloride is substituted for the cyanogen bromide and yields the formula I 2-(1-substituted-2-imidazolin-2yl)benzoate or nicotinate with an (o-nitrophenyl)thio substituent on the 1-position of the imidazolinone. The reactions may be illustrated as follows:

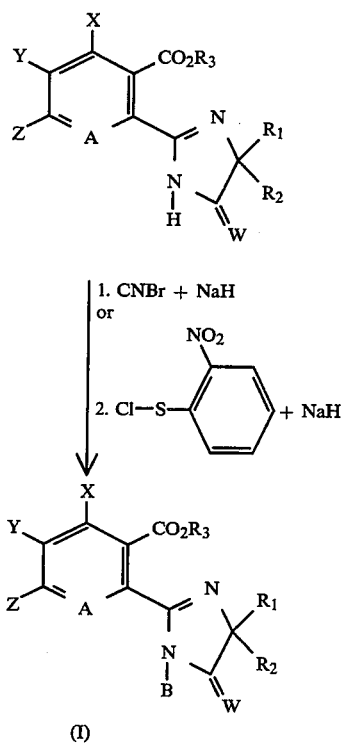

wherein X, Y, Z, A, $R_1$, $R_2$ and $R_3$ are as described for formula I with the proviso that $R_3$ cannot be hydrogen or a cation and B is (1) cyano or (2) (o-nitrophenyl)thio.

2-(1-Chloro-2-imidazolin-2-yl)benzoates and nicotinates of formula I can be prepared by the reaction of the appropriately substituted imidazolinyl benzoate or nicotinate with a suitable chlorinating agent such as tert-butyl hypochlorite. This reaction provides the desired 2-(1-chloro-2-imidazolin-2-yl)benzoate or nicotinate having the same substituents as the starting material, but in addition is substituted on the 1-position of the imidazolinone with a chlorine. The reaction may be illustrated as follows:

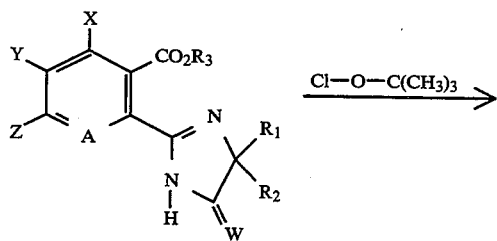

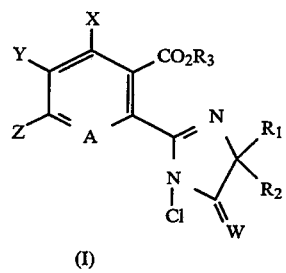

wherein X, Y, Z, A, $R_1$, $R_2$ and $R_3$ are as described for formula I with the proviso that $R_3$ cannot be hydrogen or a cation.

The formula I 2-(1-substituted-2-imidazolin-2-yl)benzoic and nicotinic acids, and derivatives thereof, of the present invention are effective herbicidal agents useful for the control of a wide variety of undesirable plant species. These compounds are effective for controlling weeds native to both dry land and wet land areas. The compounds are also useful as aquatic herbicides and are effective in controlling the above-said plants when applied to the foliage thereof or to soil or water containing seeds or other propagating organs of said plants such as stolons, tubers or rhizomes, at rates of from about 0.016 to 4.0 kg/ha and preferably from about 0.125 to 4.0 kg/ha.

The formula I 2-(1-substituted-2-imidazolin-2-yl)benzoic and nicotinic acids and derivatives thereof can be formulated as emulsifiable concentrates, wettable powders, granular formulations, flow concentrates and the like.

In order to facilitate a further understanding of the invention, the following examples are presented primarily for the purpose of illustrating more specific details thereof. The invention is not to be deemed limited thereby except as defined in the claims.

EXAMPLE 1

Preparation of Methyl phthaladehydate, 2-oxime

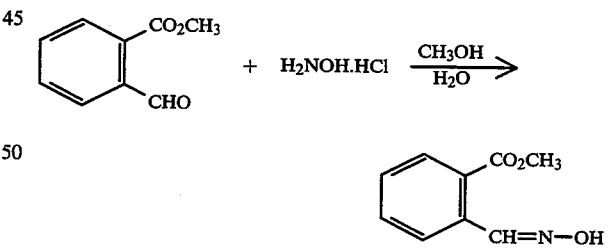

Hydroxylamine hydrochloride (4.26 g, 0.0609 mol) is added to a solution of methyl phthalaldehydate (10.0 g, 0.0609 mol) in aqueous methanol (180 mL H$_2$O/420 mL methanol) at 10°–15° C. under a nitrogen stream. The resulting solution is stirred for 1¼ hours at 10°–15° C., 1¼ hours at 5°–10° C. and then the reaction mixture is concentrated in vacuo to remove the methanol. Methylene chloride is added to the aqueous residue. The methylene chloride layer is separated, dried over anhydrous magnesium sulfate and concentrated in vacuo to give the title compound as a white solid (10.5 g, 91%), mp 55°–65° C., identified by IR and NMR spectral analyses.

Following the procedure described in example 1, but using the appropriately substituted methyl nicotinate or methyl benzoate, the compounds shown below are obtained.

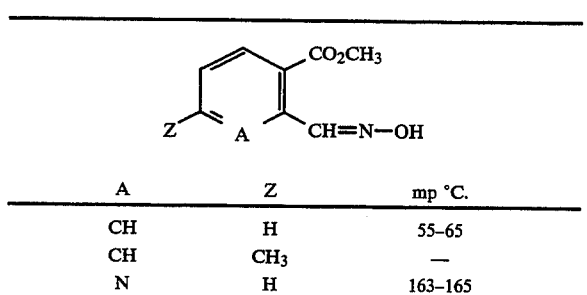

| A  | Z   | mp °C.  |
|----|-----|---------|
| CH | H   | 55–65   |
| CH | CH₃ | —       |
| N  | H   | 163–165 |

EXAMPLE 2

Preparation of Methyl o-(chloroformyl)benzoate, o-oxime

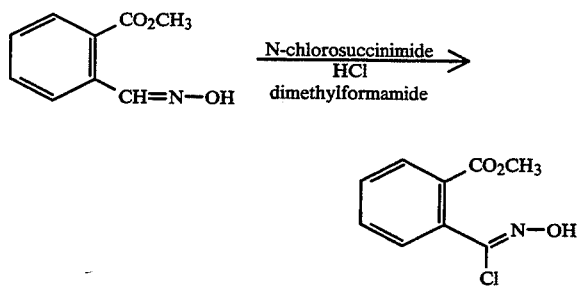

To a solution of methyl phthaladehydate, 2-oxime (9.85 g, 0.055 mol) and dimethylformamide under a nitrogen stream is added portionwise N-chlorosuccinimide (7.34 g, 0.055 mol) and hydrochloric acid is bubbled into the reaction mixture for 15 seconds. The N-chlorosuccinimide is added at such a rate as to keep the reaction mixture temperature below 35° C. The reaction mixture is stirred for 20 minutes, cooled to 10° C., poured into cold water and extracted with ether. The combined ether extracts are diluted with hexanes, washed sequentially with dilute hydrochloric acid solution, water and brine, dried over anhydrous magnesium sulfate and concentrated in vacuo to give the title compound as a white solid (8.7 g, 70%), identified by IR and NMR spectral analyses.

Following the procedure for example 2, but using the appropriately substituted oxime, the compounds shown below are obtained.

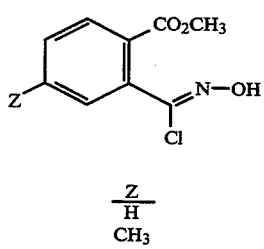

| Z   |
|-----|
| H   |
| CH₃ |

EXAMPLE 3

Preparation of Methyl 2,3-dimethyl-2-[(1-oxo-2,3-benzoxazin-4-yl)amino]butyrate

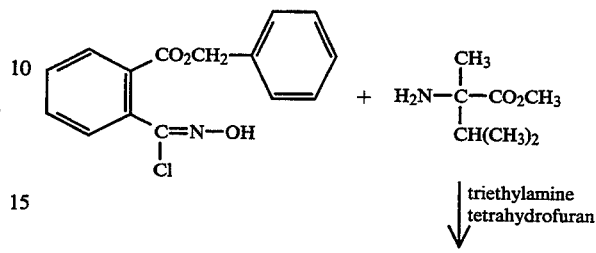

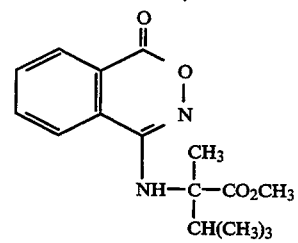

A solution of methyl 2-amino-2,3-dimethyl-butyrate (2.76 g, 0.019 mol), and triethylamine (1.97 g, 0.0195 mol) and tetrahydrofuran is added dropwise to a 5° C. mixture of benzyl o-(chloroformyl)benzoate, o-oxime (6.0 g, 0.02 mol) (which is prepared following the procedure in examples 1 and 2) and tetrahydrofuran under a nitrogen stream. The reaction mixture is stirred at room temperature for 21 hours, filtered to remove solids and the filtrate is concentrated in vacuo to give a yellow oil. The oil is dissolved into methylene chloride. The methylene chloride solution is washed sequentially with water and brine, dried over anhydrous magnesium sulfate and concentrated in vacuo to give a yellow oil. Crystallization of the oil from a benzene/hexanes/methylene chloride solution yields a white solid. The solid is chromatographed using neutral alumina and 4% ethyl acetate in methylene chloride as eluent to give the title compound as a white solid (2.41 g, 40%), mp 132°–134°, identified by IR and NMR spectral analyses.

Following the procedure of example 3, but using the appropriately substituted amino methyl ester and the appropriate oxime, the following compounds are obtained.

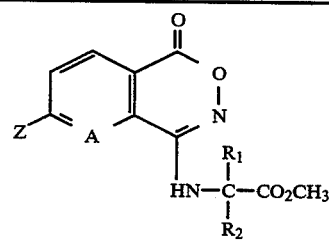

| A  | Z   | R₁              | R₂       | mp °C.  |
|----|-----|-----------------|----------|---------|
| CH | H   | CH₃             | CH(CH₃)₂ | 132–134 |
| CH | CH₃ | CH₃             | CH(CH₃)₂ | 190–191 |
| N  | H   | CH₃             | CH(CH₃)₂ | 92–96   |
| CH | H   | —(CH₂)₅—        |          | 162–168 |

EXAMPLE 4

Preparation of
o(1-Hydroxy-4-isopropyl-4-methyl-5-oxo-2-imidazolin-2-yl)benzoic acid

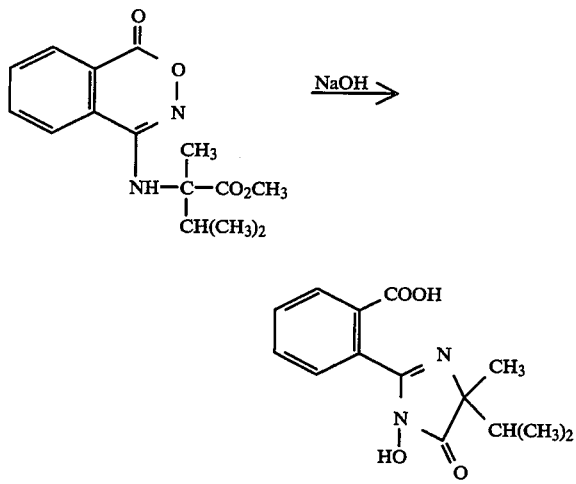

Sodium hydroxide (0.58 g, 0.0145 mol) in water is added to a solution of methyl 2,3-dimethyl-2-[(1-oxo-2,3-benzoxazin-4-yl)amino]butyrate (2.0 g, 0.00689 mol) and tetrahydrofuran under a nitrogen atmosphere. The reaction mixture is stirred at 45° C. for 36 hours then at room temperature for 6 days. The reaction mixture is concentrated in vacuo to give an oil. The oil is dissolved into water. The aqueous solution is cooled with an ice-bath and concentrated sulfuric acid is added until a pH of about 1 is obtained then the solution is extracted with ethyl acetate. The combined ethyl acetate extracts are dried with anhydrous magnesium sulfate and concentrated in vacuo to give a pale yellow solid. The solid is added to boiling methylene chloride and after 2/3 of the methylene chloride has evaporated, the mixture is filtered to give the title compound as a white solid (1.44 g, 76%), mp 186°–188° C., identified by IR and NMR spectral analyses.

Following the procedure of example 4, but using the appropriately substituted methyl ester, the following compounds are obtained.

| A | Z | $R_1$ | $R_2$ | mp °C. |
|---|---|---|---|---|
| CH | H | $CH_3$ | $CH(CH_3)_2$ | 186–188 |
| N | H | $CH_3$ | $CH(CH_3)_2$ | 146–150 |
| CH | H | —$(CH_2)_5$— | | 161–169 |
| CH | $CH_3$ | $CH_3$ | $CH(CH_3)_2$ | 199–200 |

EXAMPLE 5

Preparation of Methyl
o-(1-hydroxy-4-isopropyl-4-methyl-5-oxo-2-imidazolin-2-yl)benzoate

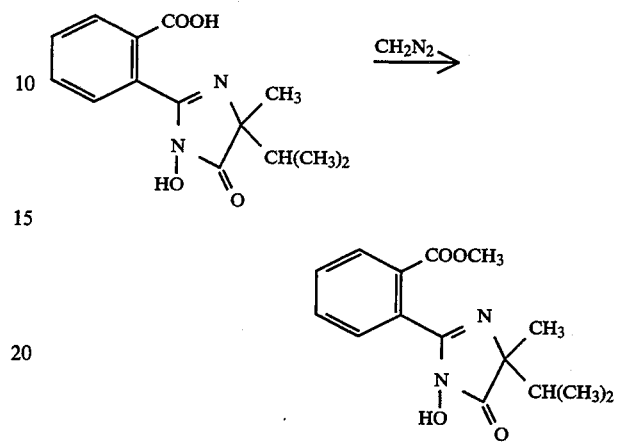

A solution of potassium hydroxide (0.19 g, 0.00339 mol) and ethanol is added portionwise to a 0° C. mixture of Diazald® N-methyl-N-nitroso-D-toluenesulfonamide (0.73 g, 0.0034 mol) and ether. The mixture is kept in an ice-bath for 10 minutes then in an water bath for 10 minutes. The diazomethane is distilled into a mixture of o-(1-hydroxy-4-isopropyl-4-methyl-5-oxo-2-imidazolin-2-yl)benzoic acid (0.67 g, 0.00243 mol) and ethanol. After 45 minutes the reaction mixture is quenched with acetic acid and concentrated in vacuo to give an oil. The oil is dissolved into ethyl acetate, dried over anhydrous magnesium sulfate and concentrated in vacuo to yield an off-white solid. The solid is chromatographed using silica gel and methylene chloride/ethyl acetate 3:1 as eluent to give the title compound as a white solid (0.18 g, 26%), mp 146°–150° C., identified by IR and NMR spectral analyses.

Following the procedure of example 5, but using the appropriately substituted benzoic acid or nicotinic acid, the following compounds are obtained.

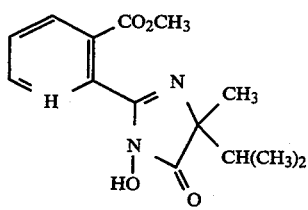

| A | mp °C. |
|---|---|
| CH | 146–150 |
| N | 164–168 |

EXAMPLE 6

Preparation of Methyl 2-(chloroformyl)nicotinate, 2-oxime, hydrochloride

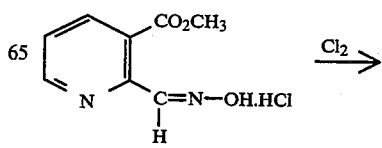

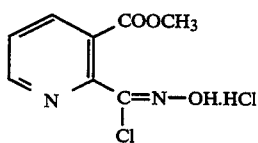

Chlorine is bubbled into a −40° C. mixture of methyl 2-formyl nicotinate (1.6 g, 0.00739 mol) and tetrahydrofuran for 20 minutes. The reaction mixture is warmed to room temperature and stirred for 2 hours. Filtration of the mixture gives the title compound as a white solid (2.18 g, 100%), mp 147° C., identified by IR and NMR spectral analyses.

EXAMPLE 7

Preparation of Methyl o-(4-isopropyl-4-methyl-1-[(o-nitrophenyl)thio]-5-oxo-2-imidazolin-2-yl)benzoate

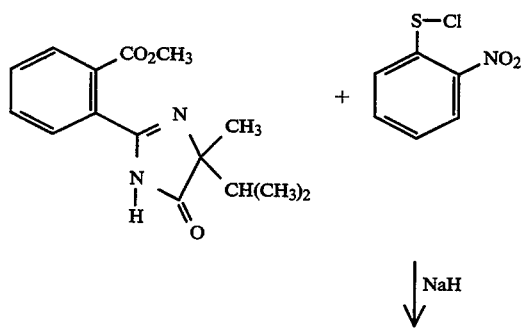

A slurry of sodium hydride (0.76 g, 0.019 mol, 60% in mineral oil) and tetrahydrofuran is added dropwise to a 0° C. solution of methyl o-(4-isopropyl-4-methyl-5-oxo-2-imidazolin-2-yl)benzoate (5.0 g, 0.018 mol) and tetrahydrofuran under a nitrogen atmosphere. After stirring for 1 hour at room temperature, 2-nitrobenzenesulfinyl chloride (3.8 g, 0.020 mol) is added dropwise to the mixture and stirring is continued at room temperature for 72 hours. The reaction mixture is filtered and the filtrate is concentrated in vacuo to give a yellow solid. The solid is chromatographed using silica gel and 10% ethyl acetate in methylene chloride as eluent to yield the title compound as a pale yellow solid (1.08 g, 14%, mp 143°–148° C., identified by IR and NMR spectral analyses.

Following the procedure of example 7, but using the appropriately substituted nicotinate or benzoate and the appropriate electrophile, the compounds shown below are obtained.

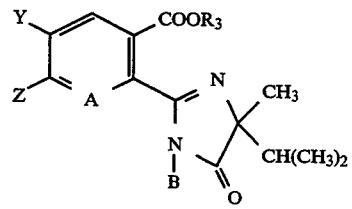

| A | B | R₃ | Y | Z | mp °C. |
|---|---|---|---|---|---|
| CH | NO₂ (—S—phenyl with NO₂) | CH₃ | H | H | 143–148 |
| N | —P(=O)(OCH₂CH₃)₂ | CH₃ | CH₃ | H | — |
| N | —P(=O)(OCH₂CH₃)₂ | CH₃ | H | H | 67–71 |
| N | NO₂ (—S—phenyl with NO₂) | —(CH₂)₂Si(CH₃)₃ | H | H | 150–151 |
| CH | CN | CH₃ | H | H | — |
| N | CN | CH₃ | H | H | — |
| N | CN | —(CH₂)₂Si(CH₃)₃ | CH₃ | H | 129–130 |

-continued

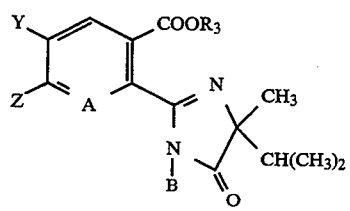

| A | B | R₃ | Y | Z | mp °C. |
|---|---|---|---|---|---|
| N | CN | —CH₂—C₆H₄—OCH₃ | CH₂CH₃ | H | — |
| N | CN | —(CH₂)₂Si(CH₃)₃ | CH₂CH₃ | H | 53–55 |
| N | CN | —(CH₂)₂Si(CH₃)₃ | H | H | 91–92 |
| N | CN | —CH₂CH=CH—C₆H₅ | CH₃ | H | 81–83 |
| N | CN | —(CH₂)₂Si(CH₃)₃ | CH₂OCH₃ | H | — |
| N | CN | —CH₂-furyl | CH₂CH₃ | H | — |
| N | CN | —CH₂-(3,4-methylenedioxyphenyl) | CH₃ | H | 147–149 |
| N | CN | —CH₂—C₆H₅ | H | H | — |
| CH | CN | CH₃ | H | CH₃ | — |
| CH | CN | CH₃ | CH₃ | H | — |
| N | CN | —CH₂CH=CH₂ | CH₃ | H | 88–92 |
| N | CN | CH₃ | OCH₃ | H | — |
| N | CN | CH₃ | CH₃ | H | — |
| N | CN | —CH₂—C₆H₄—OCH₃ | CH₃ | H | — |
| N | CN | ⁺N[(CH₂)₃CH₃]₄ | —CH=CH—CH=C— | | 62–68 |
| N | CN | —(CH₂)₂Si(CH₃)₃ | —CH=CH—CH=C— | | 161–163 |
| N | CN | CH₂CH=CH₂ | —CH=CH—CH=C— | | 98–100 |
| N | —S—(2-NO₂-C₆H₄) | CH₃ | H | H | 155–156 |
| N | —S—(2-NO₂-C₆H₄) | CH₃ | CH₃ | H | 150–151 |

-continued

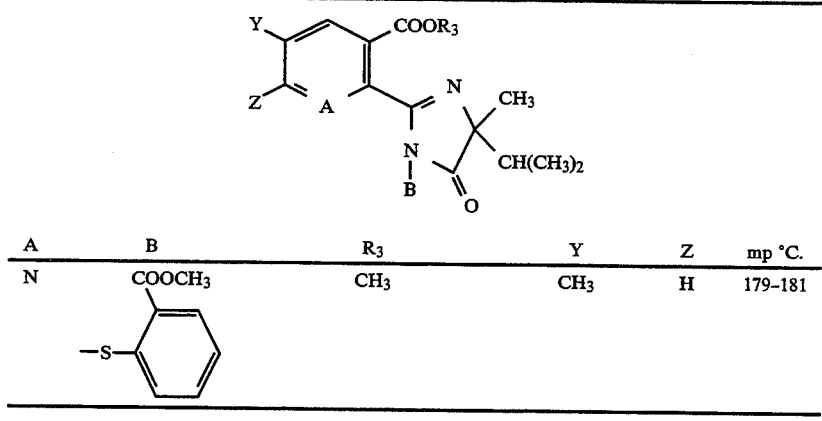

| A | B | R₃ | Y | Z | mp °C. |
|---|---|---|---|---|---|
| N | COOCH₃ (—S—phenyl with COOCH₃) | CH₃ | CH₃ | H | 179–181 |

EXAMPLE 8

Preparation of Tetrabutylammonium 2-(1-cyano-4-isopropyl-4-methyl-5-oxo-2-imidazolin-2-yl)nicotinate

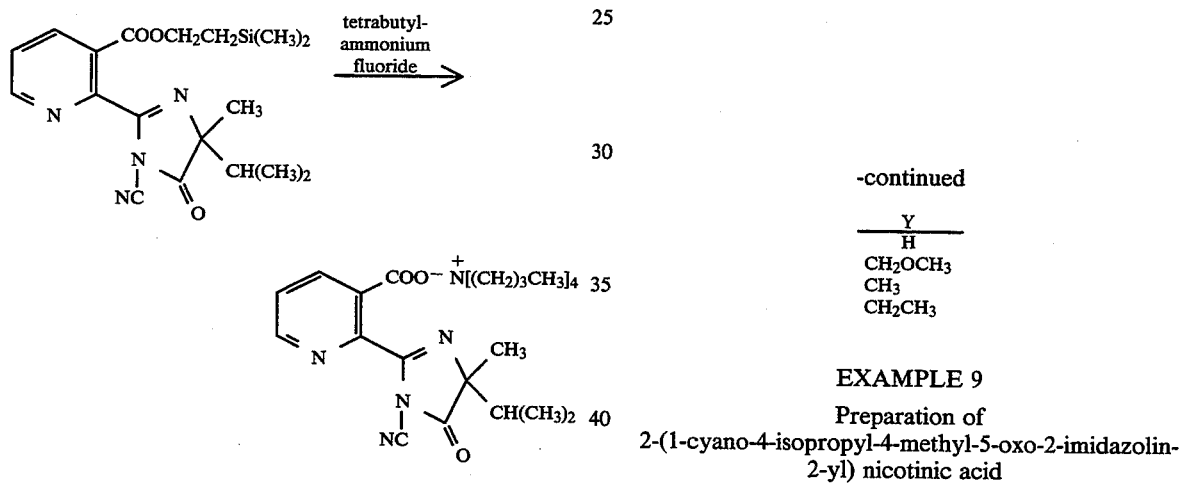

To a solution of 2-(trimethylsilyl)ethyl 2-(1-cyano-4-isopropyl-4-methyl-5-oxo-2-imidazolin-2-yl)nicotinate (7.74 g, 0.02 mol) and tetrahydrofuran is added tetrabutylammonium fluoride (0.020 mol, 1.0M, 20.0 mL). The reaction mixture is stirred at room temperature for 72 hours, concentrated in vacuo to an oil and the oil is dissolved into methylene chloride. The methylene chloride solution is washed sequentially with water and brine, dried over anhydrous magnesium sulfate and concentrated in vacuo to give the title compound as a dark yellow syrup (8.7 g, 82%), identified by IR and NMR spectral analyses.

Following the procedure of example 8, but using the appropriately substituted 2-(trimethylsilyl)ethyl 2-(1-cyano-4-isopropyl-4-methyl-5-oxo-2-imidazolin-2-yl)nicotinate, the following compounds are obtained.

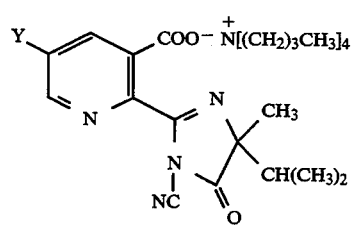

-continued

| Y |
|---|
| H |
| CH₂OCH₃ |
| CH₃ |
| CH₂CH₃ |

EXAMPLE 9

Preparation of 2-(1-cyano-4-isopropyl-4-methyl-5-oxo-2-imidazolin-2-yl) nicotinic acid Tetrabutylammonium 2-(1-cyano-4-isopropyl-4-methyl-5-oxo-2-imidazolin-2-yl)nicotinate (0.36 g, 0.00068 mol) is placed into a mixture of cyclohexane and ethyl acetate for 3 months. The mixture is filtered to yield the title compound as a tan solid (0 09 g 42%) mp 150°–153° C. identified by IR and NMR spectral analyses.

EXAMPLE 10

Preparation of Methyl 2-(1-chloro-4-isopropyl-4-methyl-5-oxo-2-imidazolin-2-yl)nicotinate

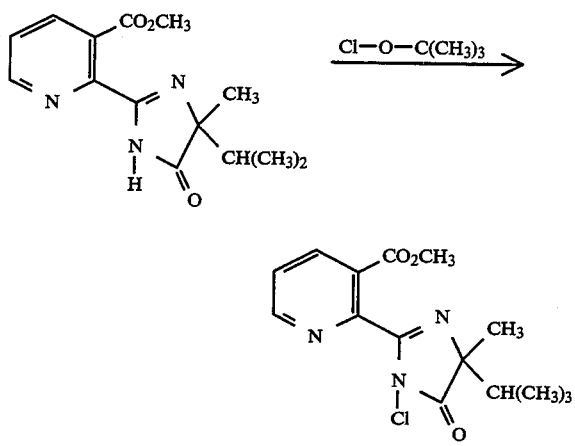

Tert-butyl hypochlorite (5.92 g, 0.0545 mol) is added to a solution of methyl 2-(4-isopropyl-4-methyl-5-oxo-2-imidazolin-2-yl)nicotinate (10.0 g, 0.0363 mol) and methanol. The reaction mixture is covered with foil and stirring is continued for 1 day. The reaction mixture is concentrated in vacuo to give a liquid. The liquid is dissolved into methylene chloride, dried over anhydrous magnesium sulfate and concentrated in vacuo to yield a yellow syrup. The yellow syrup is chromatographed using silica gel and 5% ethyl acetate in hexanes as eluent to give the title compound as a colorless syrup (7.16 g, 64%), identified by IR and NMR spectral analyses.

Following the procedure of example 10, but using the appropriate nicotinate, the compounds shown below are obtained.

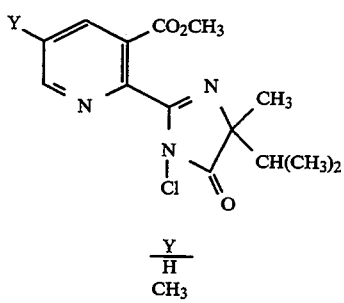

| Y |
|---|
| H |
| CH₃ |

EXAMPLE 11

Preemergence herbicidal evaluation of test compounds

The preemergence herbicidal activity of the compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.016 to 8.0 kg per hectare of test compound per cup. The treated cups are then placed on greenhouse benches, watered and cared for in accordance with conventional greenhouse procedures. From four to five weeks after treatment, the tests are terminated and each cup is examined and rated according to the rating system set forth below. Data obtained are reported in Table I below. Where more than one test is involved for a given compound, the data are averaged.

Plant species employed in these evaluations are reported by header abbreviation, common name and scientific name.

Compounds employed in this preemergence herbicidal evaluation and in the post-emergence evaluation in the following example are given a compound number and identified by name. Data in Table I are reported by compound number.

Herbicide Rating Scale

Results of herbicide evaluation are expressed on a rating scale (0-9). The scale is based upon a visual observation of plant stand, vigor, malformation, size, chlorosis and overall plant appearance as compared with a control.

| Rating | Meaning | % Control Compared To Check |
|---|---|---|
| 9 | Complete Kill | 100 |
| 8 | Approaching Complete kill | 91-99 |
| 7 | Good Herbicidal Effect | 80-90 |
| 6 | Herbicidal Effect | 65-79 |
| 5 | Definite Injury | 45-64 |
| 4 | Injury | 30-44 |
| 3 | Moderate Effect | 16-29 |
| 2 | Slight Effect | 6-15 |
| 1 | Trace Effect | 1-5 |
| 0 | No Effect | 0 |

PLANT SPECIES EMPLOYED IN HERBICIDAL EVALUATIONS

| HEADER ABB | COMMON NAME | SCIENTIFIC NAME |
|---|---|---|
| BARNYARDGR | BARNYARDGRASS | ECHINOCHLOA.CRUS-GALLI, (L)BEAU |
| FOXTAIL SP | FOXTAIL SPP. | SETARIA SPP. |
| P NUTSEDGE | NUTSEDGE, PURPLE | CYPERUS RONTUNDUS, L. |
| WILD OATS | OAT, WILD | AVENA FATUA, L. |
| QUACKGRASS | QUACKGRASS | AGROPYRON REPENS, (L)BEAUV |
| FLD BINDWD | BINDWEED, FIELD (RHIZOME) | CONVOLVULUS ARVENSIS, L. |
| MRNGLRY SP | MORNINGGLORY SPP. | IPOMOEA SPP. |
| WILD MUSTD | MUSTARD, WILD | BRASSICA KABER, (DC)L.C.WHEELR |
| VELVETLEAF | VELVETLEAF | ABUTILON THEOPHRASTI, MEDIC. |

| HEADER ABB | COMMON NAME | SCIENTIFIC NAME |
| --- | --- | --- |
| WHT FENMAN | WHEAT, FENMAN | *TRITICUM AESTIVUM, FENMAN* |
| SUGARBEETS | SUGARBEETS | *BETA VULGARIS, L.* |
| CORN FIELD, | CORN, FIELD | *ZEA MAYS., L.* |
| COTTON | COTTON | *GOSSYPIUM HIRSUTUM, L.* |
| SOYBEAN | SOYBEAN | *GLYCINE MAX* |

COMPOUNDS EVALUATED AS HERBICIDAL AGENTS

| Compound No. | |
| --- | --- |
| 1 | o-(1-Hydroxy-4-isopropyl-4-methyl-5-oxo-2-imidazolin-2-yl)benzoic acid |
| 2 | o-(3-Hydroxy-4-oxo-1,3-diazaspiro[4.5]-dec-1-en-2-yl)benzoic acid |
| 3 | 2-(1-Hydroxy-4-isopropyl-4-methyl-5-oxo-2-imidazolin-2-yl)nicotinic acid |
| 4 | Methyl 2-(1-hydroxy-4-isopropyl-4-methyl-5-oxo-2-imidazolin-2-yl)-nicotinate |
| 5 | 2-(1-Hydroxy-4-isopropyl-4-methyl-5-oxo-2-imidazolin-2-yl)-p-toluic acid |
| 6 | Methyl o-(1-hydroxy-4-isopropyl-4-methyl-5-oxo-2-imidazolin-2-yl)benzoate |
| 7 | Methyl o-(1-cyano-4-isopropyl-4-methyl-5-oxo-2-imidazolin-2-yl)benzoate |
| 8 | Methyl 2-(1-cyano-4-isopropyl-4-methyl-5-oxo-2-imidazolin-2-yl)nicotinate |
| 9 | Methyl 2-(1-cyano-4-isopropyl-4-methyl-5-oxo-2-imidazolin-2-yl)-5-methylnicotinate |
| 10 | 2-(Trimethylsilyl)ethyl 2-{4-isopropyl-4-methyl-1-[(o-nitrophenyl)thio]-5-oxo-2-imidazolin-2-yl}nicotinate |
| 11 | Methyl o-{4-isopropyl-4-methyl-1-[o-nitrophenyl)thio]-5-oxo-2-imidazolin-2-yl}benzoate |
| 12 | Methyl 2-(4-isopropyl-4-methyl-5-oxo-1-phosphono-2-imidazolin-2-yl)nicotinate, P,P-diethyl |
| 13 | Methyl 2-(4-isopropyl-4-methyl-5-oxo-1-phosphono-2-imidazolin-2-yl)-5-methyl-nicotinate, P,P-diethyl |
| 14 | 2-(Trimethylsilyl)ethyl 2-(1-cyano-4-isopropyl-4-methyl-5-oxo-2-imidazolin-2-yl)-5-methylnicotinate |
| 15 | p-Methoxybenzyl 2-(1-cyano-4-isopropyl-4-methyl-5-oxo-2-imidazolin-2-yl)-5-ethylnicotinate |
| 16 | Furfuryl 2-(1-cyano-4-isopropyl-4-methyl-5-oxo-2-imidazolin-2-yl)-5-ethylnicotinate |
| 17 | 2-(Trimethylsilyl)ethyl 2-(1-cyano-4-isopropyl-4-methyl-5-oxo-2-imidazolin-2-yl)-5-ethylnicotinate |
| 18 | Tetrabutylammonium 2-(1-cyano-4-isopropyl-4-methyl-5-oxo-2-imidazolin-2-yl)-5-methylnicotinate |
| 19 | Allyl 2-(1-cyano-4-isopropyl-4-methyl-5-oxo-2-imidazolin-2-yl)-3-quinoline-carboxylate |
| 20 | Tetrabutylammonium 2-(1-cyano-4-isopropyl-4-methyl-5-oxo-2-imidazolin-2-yl)-5-ethylnicotinate |
| 21 | Allyl 2-(1-cyano-4-isopropyl-4-methyl-5-oxo-2-imidazolin-2-yl)-5-methyl-nicotinate |
| 22 | p-Methoxybenzyl 2-(1-cyano-4-isopropyl-4-methyl-5-oxo-2-imidazolin-2-yl)-5-methylnicotinate |
| 23 | Methyl 2-(1-cyano-4-isopropyl-4-methyl-5-oxo-2-imidazolin-2-yl)-5-methoxy-nicotinate |
| 24 | 2-(Trimethylsilyl)ethyl 2-(1-cyano-4-isopropyl-4-methyl-5-oxo-2-imidazolin-2-yl)nicotinate |
| 25 | Tetrabutylammonium 2-(1-cyano-4-isopropyl-4-methyl-5-oxo-2-imidazolin-2-yl)-3-quinolinecarboxylate |
| 26 | Methyl 2(and 6)-(1-cyano-4-isopropyl-4-methyl-5-oxo-2-imidazolin-2-yl)-p(and m)-toluate, (3:2) |
| 27 | Methyl 2-(1-chloro-4-isopropyl-4-methyl-5-oxo-2-imidazolin-2-yl)-nicotinate |
| 28 | Methyl 2-(1-chloro-4-isopropyl-4-methyl-5-oxo-2-imidazolin-2-yl)-5-methylnicotinate |
| 29 | Tetrabutylammonium 2-(1-cyano-4-isopropyl-4-methyl-5-oxo-2-imidazolin-2-yl)nicotinate |
| 30 | Cinnamyl 2-(1-cyano-4-isopropyl-4-methyl-5-oxo-2-imidazolin-2-yl)-5-methylnicotinate |
| 31 | Benzyl 2-(1-cyano-4-isopropyl-4-methyl-5-oxo-2-imidazolin-2-yl)-nicotinate |
| 32 | Piperonyl 2-(1-cyano-4-isopropyl-4-methyl-5-oxo-2-imidazolin-2-yl)-5-methylnicotinate |
| 33 | Tetrabutylammonium 2-(1-cyano-4-isopropyl-4-methyl-5-oxo-2-imidazolin-2-yl)-5-(methoxymethyl)nicotinate |
| 34 | Methyl 2-{4-isopropyl-4-methyl-1-[(o-nitrophenyl)thio]-5-oxo-2-imidazolin-2-yl}nicotinate |
| 35 | Methyl 2-{4-isopropyl-4-methyl-1-[(o-nitrophenyl)thio]-5-oxo-2-imidazolin-2-yl}-5-methylnicotinate |
| 36 | Nicotinic acid, 2-{1-[(o-carboxyphenyl)-thio]-4-isopropyl-4-methyl-5-oxo-2-imidazolin-2-yl}-5-methyl-, dimethyl ester |

TABLE I

PRE-EMERGENCE TESTS - RATES IN KG/HA

| Compound No | RATE | BARNY ARDGR | FOXTA IL SP | P NUT SEDGE | WILD OATS | QUACK GRASS | FLD B INDWD | MRNGL RY SP | WILD MUSTD | VELVE TLEAF | WHT F ENMAN | SUGAR BEETS | CORN FIELD | COTTON | SOYBE AN WI |
|---|---|---|---|---|---|---|---|---|---|---|---|---|---|---|---|
| 1 | 1.000 | 5.0 | 9.0 | 9.0 | 3.7 | 9.0 | 9.0 | 7.7 | 9.0 | 8.7 | 6.0 | 9.0 | 7.3 | 8.7 | 7.0 |
|   | .500 | 4.7 | 6.5 | 9.0 | 3.0 | 8.7 | 9.0 | 6.7 | 9.0 | 7.3 | 5.3 | 9.0 | 7.0 | 8.0 | 6.5 |
|   | .250 | 2.0 | 1.5 | 8.7 | 1.3 | 9.0 | 7.0 | 6.0 | 9.0 | 6.3 | 2.5 | 8.3 | 5.3 | 7.0 | 4.3 |
|   | .125 | 1.7 | 1.0 | 7.7 | 0.0 | 5.3 | 4.3 | 5.0 | 9.0 | 4.3 | 0.0 | 6.7 | 3.0 | 7.0 | 2.0 |
| 2 | 1.000 | 2.0 |   | 6.0 | 1.0 | 1.0 | 7.0 | 6.0 | 9.0 | 5.0 |   | 8.0 | 0.0 | 7.0 | 5.0 |
|   | .500 | 0.0 |   | 5.0 | 0.0 | 0.0 | 1.0 | 5.0 | 7.0 | 4.0 |   | 3.0 | 1.0 | 3.0 | 4.0 |
|   | .250 | 0.0 |   | 2.0 | 1.0 | 0.0 | 0.0 | 3.0 | 5.0 | 2.0 |   | 3.0 | 0.0 | 3.0 | 2.0 |
|   | .125 | 0.0 |   | 0.0 | 0.0 | 0.0 | 0.0 | 0.0 | 3.0 | 1.0 |   | 2.0 | 0.0 | 4.0 | 2.0 |
| 3 | .500 | 9.0 | 9.0 | 9.0 | 9.0 | 9.0 | 9.0 | 8.0 | 0.0 | 8.0 | 9.0 | 9.0 | 0.0 | 9.0 | 8.0 |
|   | .250 | 8.0 | 9.0 | 9.0 | 9.0 | 9.0 | 9.0 | 8.0 |   | 8.0 | 8.0 | 9.0 | 9.0 | 9.0 | 8.0 |
|   | .125 | 9.0 | 9.0 | 9.0 | 9.0 | 9.0 | 9.0 | 9.0 |   | 8.0 | 8.0 | 9.0 | 9.0 | 9.0 | 7.0 |
| 4 | .500 | 9.0 | 9.0 | 9.0 | 8.0 | 9.0 | 9.0 | 9.0 |   | 8.0 | 7.0 | 9.0 | 9.0 | 7.0 | 7.0 |
|   | .250 | 3.0 | 6.0 | 9.0 | 6.0 | 9.0 | 9.0 | 7.0 |   | 8.0 | 5.0 | 9.0 | 8.0 | 7.0 | 7.0 |
| 5 | 1.000 | 5.0 | 6.0 | 6.0 | 5.0 | 9.0 | 9.0 | 7.0 | 8.0 | 8.0 | 3.0 | 9.0 | 6.0 | 7.0 | 8.0 |
|   | .500 | 3.0 | 4.0 | 7.0 | 5.0 | 9.0 | 8.0 | 7.0 | 7.0 | 8.0 | 2.0 | 9.0 | 3.0 | 5.0 | 6.0 |
|   | .250 | 5.0 | 2.0 | 4.0 | 1.0 | 9.0 | 9.0 | 5.0 | 5.0 | 7.0 | 3.0 | 9.0 | 3.0 | 4.0 | 5.0 |
|   | .125 | 3.0 | 1.0 | 6.0 | 0.0 | 7.0 | 8.0 | 1.0 | 3.0 | 7.0 | 2.0 | 9.0 | 3.0 | 3.0 | 2.0 |
| 6 | .250 | 1.0 | 0.0 | 9.0 | 0.0 | 9.0 | 9.0 | 1.0 | 0.0 | 4.0 | 0.0 | 9.0 | 3.0 | 9.0 |   |
|   | .125 | 0.0 | 0.0 | 6.0 | 0.0 | 8.0 | 9.0 | 0.0 | 5.0 | 3.0 | 4.0 | 9.0 | 2.0 | 0.0 |   |
| 7 | 1.000 | 0.0 | 0.0 | 0.0 | 0.0 | 9.0 | 5.0 | 0.0 | 5.0 | 7.0 | 2.0 | 9.0 | 1.0 | 4.0 |   |
|   | .500 | 3.0 | 2.0 | 8.0 | 8.0 | 9.0 | 9.0 | 8.0 | 5.0 | 7.0 | 1.0 | 9.0 | 6.0 | 8.0 | 7.0 |
|   | .250 | 2.0 | 1.0 | 7.0 | 7.0 | 2.0 | 9.0 | 7.0 | 9.0 | 5.0 |   | 9.0 | 5.0 | 7.0 | 6.0 |
|   | .125 | 1.0 | 0.0 | 7.0 | 5.0 | 0.0 | 2.0 | 6.0 | 7.0 | 5.0 |   | 9.0 | 4.0 | 6.0 | 5.0 |
| 8 | .500 | 0.0 | 0.0 | 6.0 | 9.0 | 0.0 | 9.0 | 4.0 | 6.0 | 4.0 | 9.0 | 7.0 | 2.0 | 5.0 | 5.0 |
|   | .250 | 9.0 | 9.0 | 9.0 | 9.0 | 9.0 | 9.0 | 9.0 | 0.0 | 9.0 | 9.0 | 9.0 | 9.0 | 9.0 | 8.0 |
|   | .125 | 9.0 | 9.0 | 9.0 | 9.0 | 9.0 | 6.0 | 9.0 | 0.0 | 9.0 | 9.0 | 9.0 | 9.0 | 9.0 | 9.0 |
| 9 | .500 | 8.5 | 9.0 | 9.0 | 8.5 | 9.0 | 5.0 | 9.0 | 5.0 | 9.0 | 9.0 | 9.0 | 9.0 | 8.5 | 8.5 |
|   | .250 | 7.5 | 9.0 | 9.0 | 8.5 | 9.0 | 9.0 | 9.0 | 4.5 | 7.0 | 7.5 | 9.0 | 9.0 | 9.0 | 8.0 |
|   | .125 | 4.5 | 8.0 | 4.0 | 4.0 | 5.0 | 9.0 | 8.5 | 8.0 | 7.0 | 5.0 | 8.3 | 8.5 | 9.0 | 8.0 |
| 10 | .500 | 7.0 | 9.0 | 4.0 | 2.0 | 8.0 | 9.0 | 7.0 | 4.5 | 6.0 | 5.0 | 8.0 | 9.0 | 4.0 | 0.0 |
|    | .250 | 7.0 | 8.0 | 4.0 | 2.0 | 8.0 | 9.0 | 5.0 | 8.0 | 7.0 | 5.0 | 8.0 | 7.0 | 0.0 | 0.0 |
|    | .125 | 4.0 | 8.0 | 4.0 | 5.0 | 6.0 | 6.0 | 4.0 | 8.0 | 7.0 | 2.0 | 8.0 | 3.0 | 0.0 | 0.0 |
| 11 | 1.000 | 1.0 | 5.0 | 3.0 | 2.0 | 0.0 | 5.0 | 5.0 | 0.0 | 7.0 |   | 8.0 | 5.0 | 7.0 | 6.0 |
|    | .500 | 0.0 | 2.0 | 4.0 | 5.0 | 0.0 | 9.0 | 3.0 | 0.0 | 6.0 |   | 7.0 | 4.0 | 6.0 | 6.0 |
|    | .250 | 1.0 | 0.0 | 3.0 | 2.0 | 0.0 | 9.0 | 5.0 | 5.0 | 5.0 |   | 4.0 | 3.0 | 5.0 | 6.0 |
|    | .125 | 0.0 | 0.0 | 1.0 | 1.0 | 0.0 | 6.0 | 3.0 | 6.0 | 4.0 |   | 9.0 | 1.0 | 4.0 | 4.0 |
| 12 | .500 | 8.0 | 9.0 | 9.0 | 9.0 | 9.0 | 9.0 | 9.0 | 9.0 | 9.0 | 9.0 | 9.0 | 9.0 | 9.0 | 8.0 |
|    | .250 | 8.0 | 9.0 | 9.0 | 9.0 | 9.0 | 9.0 | 9.0 | 9.0 | 9.0 | 9.0 | 9.0 | 9.0 | 9.0 | 8.0 |
|    | .125 | 6.0 | 9.0 | 9.0 | 9.0 | 9.0 | 8.0 | 8.0 | 9.0 | 9.0 | 9.0 | 9.0 | 9.0 | 9.0 | 8.0 |
| 13 | .500 | 8.0 | 9.0 | 9.0 | 9.0 | 9.0 | 9.0 | 8.0 | 9.0 | 9.0 | 8.0 | 9.0 | 9.0 | 9.0 | 9.0 |
|    | .250 | 8.0 | 9.0 | 7.0 | 9.0 | 8.0 | 9.0 | 6.0 | 9.0 | 8.0 | 9.0 | 9.0 | 9.0 | 9.0 | 7.0 |
|    | .125 | 2.0 | 4.0 | 7.0 | 7.0 | 0.0 | 9.0 | 8.0 | 9.0 | 7.0 | 8.0 | 7.0 | 4.0 | 6.0 | 3.0 |
| 14 | .500 | 2.0 | 4.0 | 7.0 | 4.0 | 0.0 | 7.0 | 6.0 | 5.0 | 6.0 | 4.0 | 4.0 | 4.0 | 5.0 | 1.0 |
|    | .250 | 1.0 | 2.0 | 7.0 | 2.0 | 0.0 | 9.0 | 4.0 | 6.0 | 3.0 | 1.0 | 9.0 | 3.0 | 4.0 | 0.0 |
|    | .125 | 1.0 | 0.0 | 3.0 | 0.0 | 0.0 | 9.0 | 2.0 | 9.0 | 9.0 | 1.0 | 9.0 | 1.0 | 9.0 | 0.0 |
| 15 | .500 | 9.0 | 9.0 | 9.0 | 9.0 | 9.0 | 8.0 | 7.0 | 9.0 | 9.0 | 4.0 | 9.0 | 2.0 | 2.0 | 0.0 |
|    | .250 | 8.0 | 9.0 | 9.0 | 7.0 | 9.0 | 9.0 | 5.0 | 9.0 | 8.0 | 0.0 | 9.0 | 2.0 | 7.0 | 0.0 |
|    | .125 | 7.0 | 7.0 | 7.0 | 4.0 | 9.0 | 8.0 | 7.0 | 9.0 | 9.0 | 0.0 | 9.0 | 0.0 | 4.0 | 0.0 |
| 16 | .500 | 9.0 | 9.0 | 9.0 | 6.0 | 9.0 | 9.0 | 9.0 | 9.0 | 9.0 | 8.0 | 9.0 | 8.0 | 8.0 | 0.0 |

TABLE I-continued

PRE-EMERGENCE TESTS - RATES IN KG/HA

| Compound No | RATE | BARNY ARDGR | FOXTA IL SP | P NUT SEDGE | WILD OATS | QUACK GRASS | FLD B INDWD | MRNGL RY SP | WILD MUSTD | VELVE TLEAF | WHT F ENMAN | SUGAR BEETS | CORN FIELD | COTTON | SOYBE AN WI |
|---|---|---|---|---|---|---|---|---|---|---|---|---|---|---|---|
| 17 | .250 | 8.0 | 9.0 | 9.0 | 7.0 | 9.0 | 9.0 | 9.0 | 9.0 | 8.0 | 4.0 | 9.0 | 6.0 | 7.0 | 0.0 |
|  | .125 | 6.0 | 7.0 | 9.0 | 4.0 | 7.0 | 9.0 | 9.0 | 9.0 | 7.0 | 4.0 | 9.0 | 5.0 | 4.0 | 0.0 |
|  | .500 | 2.0 | 8.0 | 7.0 | 0.0 | 6.0 | 8.0 | 2.0 | 7.0 | 9.0 | 0.0 | 8.0 | 1.0 | 3.0 | 0.0 |
|  | .250 | 0.0 | 2.0 | 6.0 | 0.0 | 2.0 | 7.0 | 1.0 | 6.0 | 8.0 | 0.0 | 8.0 | 0.0 | 1.0 | 0.0 |
|  | .125 | 0.0 | 0.0 | 6.0 | 0.0 | 2.0 | 6.0 | 0.0 | 6.0 | 2.0 | 0.0 | 7.0 | 0.0 | 0.0 | 0.0 |
| 18 | .500 | 8.0 | 9.0 | 9.0 | 8.0 | 9.0 | 9.0 | 7.0 | 8.0 | 8.0 | 9.0 | 9.0 | 8.0 | 9.0 | 7.0 |
|  | .250 | 4.0 | 9.0 | 9.0 | 6.0 | 9.0 | 9.0 | 7.0 | 8.0 | 8.0 | 8.0 | 8.0 | 7.0 | 8.0 | 6.0 |
|  | .125 | 0.0 | 7.0 | 9.0 | 2.0 | 7.0 | 9.0 | 2.0 | 9.0 | 9.0 | 4.0 | 9.0 | 6.0 | 8.0 | 3.0 |
| 19 | .250 | 6.0 | 9.0 | 9.0 | 7.0 | 9.0 | 9.0 | 4.0 | 9.0 | 8.0 | 4.0 | 8.0 | 9.0 | 9.0 | 0.0 |
|  | .125 | 7.0 | 4.0 | 7.0 | 7.0 | 7.0 | 7.0 | 0.0 | 8.0 | 7.0 | 3.0 | 9.0 | 7.0 | 7.0 | 0.0 |
| 20 | .500 | 9.0 | 9.0 | 9.0 | 9.0 | 9.0 | 9.0 | 7.5 | 9.0 | 8.0 | 9.0 | 9.0 | 8.0 | 9.0 | 0.0 |
|  | .250 | 9.0 | 9.0 | 9.0 | 8.0 | 9.0 | 9.0 | 6.5 | 9.0 | 7.5 | 7.0 | 9.0 | 7.0 | 9.0 | 0.0 |
|  | .125 | 7.0 | 9.0 | 9.0 | 7.0 | 9.0 | 9.0 | 9.0 | 9.0 | 6.5 | 6.0 | 9.0 | 6.0 | 9.0 | 0.0 |
| 21 | .500 | 8.0 | 9.0 | 9.0 | 9.0 | 9.0 | 9.0 | 9.0 | 9.0 | 9.0 | 9.0 | 9.0 | 9.0 | 9.0 | 7.0 |
|  | .250 | 7.0 | 9.0 | 9.0 | 9.0 | 9.0 | 9.0 | 8.0 | 9.0 | 9.0 | 8.0 | 9.0 | 9.0 | 9.0 | 7.0 |
| 22 | .500 | 8.0 | 9.0 | 9.0 | 9.0 | 9.0 | 9.0 | 8.0 | 9.0 | 9.0 | 9.0 | 9.0 | 9.0 | 9.0 | 7.0 |
|  | .250 | 8.0 | 9.0 | 9.0 | 9.0 | 9.0 | 9.0 | 8.0 | 9.0 | 9.0 | 7.0 | 9.0 | 9.0 | 9.0 | 9.0 |
| 23 | .500 | 7.0 | 9.0 | 9.0 | 9.0 | 9.0 | 9.0 | 8.0 | 8.0 | 9.0 | 8.0 | 9.0 | 9.0 | 9.0 | 7.0 |
|  | .250 | 9.0 | 9.0 | 9.0 | 9.0 | 7.0 | 9.0 | 8.0 | 9.0 | 9.0 | 7.0 | 9.0 | 9.0 | 9.0 | 7.0 |
|  | .125 | 9.0 | 9.0 | 9.0 | 9.0 | 7.0 | 9.0 | 8.0 | 8.0 | 9.0 | 9.0 | 9.0 | 9.0 | 9.0 | 8.0 |
| 24 | .500 | 8.0 | 8.0 | 9.0 | 9.0 | 9.0 | 9.0 | 8.0 | 9.0 | 9.0 | 9.0 | 9.0 | 9.0 | 9.0 | 8.0 |
|  | .250 | 4.0 | 7.0 | 9.0 | 9.0 | 8.0 | 7.0 | 8.0 | 9.0 | 9.0 | 9.0 | 9.0 | 9.0 | 9.0 | 8.0 |
|  | .125 | 3.0 | 8.0 | 6.0 | 7.0 | 4.0 | 7.0 | 7.0 | 8.0 | 9.0 | 9.0 | 9.0 | 9.0 | 7.0 | 7.0 |
| 25 | .500 | 2.0 | 7.0 | 8.0 | 4.0 | 9.0 | 7.0 | 4.0 | 8.0 | 8.0 | 8.0 | 9.0 | 6.0 | 7.0 | 3.0 |
|  | .250 | 4.0 | 9.0 | 8.0 | 9.0 | 6.0 | 7.0 | 6.0 | 9.0 | 6.0 | 2.0 | 9.0 | 6.0 | 6.0 | 2.0 |
| 26 | .125 | 4.0 | 3.0 | 0.0 | 8.0 | 4.0 | 7.0 | 5.0 | 9.0 | 8.0 | 1.0 | 6.0 | 9.0 | 9.0 | 0.0 |
|  | .500 | 2.0 | 4.0 | 9.0 | 7.0 | 7.0 | 4.0 | 1.0 | 9.0 | 7.0 | 1.0 | 0.0 | 0.0 | 8.0 | 7.0 |
| 27 | .250 | 0.0 | 2.0 | 0.0 | 0.0 | 0.0 | 2.0 | 0.0 | 7.0 | 0.0 | 0.0 | 0.0 | 0.0 | 7.0 | 0.0 |
|  | .125 | 6.0 | 9.0 | 9.0 | 0.0 | 9.0 | 9.0 | 8.0 | 6.0 | 0.0 | 0.0 | 0.0 | 0.0 | 0.0 | 0.0 |
| 28 | .500 | 7.0 | 8.0 | 9.0 | 9.0 | 9.0 | 9.0 | 9.0 | 9.0 | 9.0 | 9.0 | 9.0 | 9.0 | 9.0 | 8.0 |
|  | .250 | 3.0 | 8.0 | 9.0 | 9.0 | 6.0 | 9.0 | 7.0 | 9.0 | 9.0 | 9.0 | 9.0 | 9.0 | 9.0 | 8.0 |
|  | .125 | 9.0 | 9.0 | 9.0 | 9.0 | 9.0 | 9.0 | 9.0 | 9.0 | 9.0 | 9.0 | 9.0 | 9.0 | 9.0 | 8.0 |
| 29 | .500 | 9.0 | 9.0 | 9.0 | 9.0 | 9.0 | 9.0 | 8.0 | 9.0 | 9.0 | 9.0 | 9.0 | 9.0 | 9.0 | 8.0 |
|  | .250 | 9.0 | 8.0 | 9.0 | 8.0 | 9.0 | 9.0 | 8.0 | 9.0 | 9.0 | 8.0 | 9.0 | 9.0 | 8.0 | 7.0 |
|  | .125 | 8.0 | 8.0 | 9.0 | 8.0 | 9.0 | 9.0 | 6.0 | 9.0 | 8.0 | 9.0 | 9.0 | 6.0 | 8.0 | 6.0 |
| 30 | .500 | 8.0 | 8.0 | 6.0 | 9.0 | 7.0 | 9.0 | 6.0 | 9.0 | 7.0 | 8.0 | 9.0 | 4.0 | 7.0 | 6.0 |
|  | .250 | 4.0 | 4.0 | 9.0 | 2.0 | 9.0 | 9.0 | 1.0 | 8.0 | 9.0 | 9.0 | 6.0 | 0.0 | 9.0 | 0.0 |
|  | .125 | 2.0 | 2.0 | 0.0 | 0.0 | 0.0 | 9.0 | 0.0 | 7.0 | 0.0 | 0.0 | 0.0 | 0.0 | 0.0 | 0.0 |
| 31 | .500 | 6.0 | 9.0 | 9.0 | 6.0 | 9.0 | 9.0 | 8.0 | 9.0 | 9.0 | 9.0 | 9.0 | 9.0 | 9.0 | 8.0 |
|  | .250 | 7.0 | 8.0 | 9.0 | 9.0 | 6.0 | 7.0 | 9.0 | 9.0 | 9.0 | 7.0 | 9.0 | 9.0 | 9.0 | 8.0 |
|  | .125 | 3.0 | 9.0 | 9.0 | 9.0 | 9.0 | 9.0 | 8.0 | 9.0 | 9.0 | 9.0 | 9.0 | 9.0 | 9.0 | 6.0 |
| 32 | .500 | 9.0 | 9.0 | 9.0 | 9.0 | 9.0 | 9.0 | 9.0 | 9.0 | 9.0 | 8.0 | 9.0 | 9.0 | 8.0 | 6.0 |
|  | .250 | 9.0 | 9.0 | 9.0 | 8.0 | 7.0 | 9.0 | 7.0 | 9.0 | 8.0 | 5.0 | 9.0 | 4.0 | 8.0 | 5.0 |
|  | .125 | 7.0 | 9.0 | 8.0 | 6.0 | 4.0 | 6.0 | 6.0 | 9.0 | 7.0 | 9.0 | 9.0 | 9.0 | 6.0 | 3.0 |
| 33 | .500 | 6.0 | 9.0 | 9.0 | 4.0 | 7.0 | 8.0 | 7.0 | 9.0 | 8.0 | 3.0 | 9.0 | 4.0 | 6.0 | 7.0 |
|  | .250 | 8.0 | 8.0 | 9.0 | 8.0 | 4.0 | 9.0 | 8.0 | 9.0 | 9.0 | 4.0 | 9.0 | 8.0 | 6.0 | 6.0 |
|  | .125 | 8.0 | 8.0 | 9.0 | 7.0 | 4.0 | 9.0 | 6.0 | 9.0 | 7.0 | 0.0 | 9.0 | 4.0 | 6.0 | 5.0 |
|  | .500 | 8.0 | 9.0 | 9.0 | 9.0 | 9.0 | 9.0 | 9.0 | 9.0 | 9.0 | 9.0 | 9.0 | 9.0 | 9.0 | 3.0 |
|  | .250 | 8.0 | 9.0 | 9.0 | 9.0 | 9.0 | 9.0 | 8.0 | 9.0 | 9.0 | 9.0 | 9.0 | 9.0 | 9.0 | 4.0 |
|  | .125 | 8.0 | 9.0 | 9.0 | 9.0 | 9.0 | 9.0 | 6.0 | 9.0 | 9.0 | 9.0 | 9.0 | 9.0 | 6.0 | 6.0 |
|  | .500 | 8.0 | 8.0 | 9.0 | 9.0 | 9.0 | 9.0 | 9.0 | 9.0 | 8.0 | 0.0 | 9.0 | 4.0 | 6.0 | 4.0 |
|  | .250 | 8.0 | 9.0 | 9.0 | 9.0 | 9.0 | 9.0 | 0.0 | 9.0 | 9.0 | 9.0 | 9.0 | 9.0 | 9.0 | 4.0 |

TABLE I-continued

PRE-EMERGENCE TESTS - RATES IN KG/HA

| Compound No | RATE | BARNY ARDGR | FOXTAIL SP | P NUT SEDGE | WILD OATS | QUACK GRASS | FLD B INDWD | MRNGL RY SP | WILD MUSTD | VELVE TLEAF | WHT F ENMAN | SUGAR BEETS | CORN FIELD | COTTON | SOYBE AN WI |
|---|---|---|---|---|---|---|---|---|---|---|---|---|---|---|---|
| 34 | .125 | 8.0 | 9.0 | 9.0 | 9.0 | 9.0 | 9.0 | 8.0 | | 8.0 | 9.0 | 9.0 | 9.0 | 9.0 | 4.0 |
|  | .500 | 8.0 | 9.0 | 9.0 | 9.0 | 9.0 | 9.0 | 9.0 | 9.0 | 9.0 | 9.0 | 9.0 | 9.0 | 9.0 | 8.0 |
|  | .250 | 8.0 | 9.0 | 9.0 | 9.0 | 9.0 | 9.0 | 9.0 | | 9.0 | 9.0 | 9.0 | 9.0 | 9.0 | 8.0 |
|  | .125 | 5.0 | 9.0 | 9.0 | 9.0 | 9.0 | 9.0 | 9.0 | | 9.0 | 9.0 | 9.0 | 9.0 | 9.0 | 8.0 |
| 35 | .500 | 9.0 | 9.0 | 9.0 | 9.0 | 9.0 | 9.0 | 9.0 | | 8.0 | 8.0 | 9.0 | 9.0 | 9.0 | 7.0 |
|  | .250 | 9.0 | 9.0 | 9.0 | 9.0 | 9.0 | 9.0 | 8.0 | | 8.0 | 9.0 | 9.0 | 7.0 | 9.0 | 6.0 |
|  | .125 | 9.0 | 9.0 | 9.0 | 9.0 | 2.0 | 9.0 | 8.0 | | 8.0 | 7.0 | 9.0 | 9.0 | 9.0 | 5.0 |
| 36 | .500 | 9.0 | 9.0 | 9.0 | 9.0 | 9.0 | 9.0 | 9.0 | | 9.0 | 9.0 | 9.0 | 9.0 | 9.0 | 7.0 |
|  | .250 | 9.0 | 9.0 | 9.0 | 9.0 | 9.0 | 9.0 | 9.0 | | 9.0 | 8.0 | 9.0 | 9.0 | 9.0 | 6.0 |
|  | .125 | 6.0 | 9.0 | 9.0 | 9.0 | 6.0 | 9.0 | 9.0 | | 9.0 | 5.0 | 9.0 | 7.0 | 8.0 | 5.0 |

EXAMPLE 12

Postemergence herbicidal evaluation of test compounds

The postemergence herbicidal activity of the compounds of the present invention is determined by the following tests, wherein a variety of monocotyledonous and dicotyledonous plants are treated with test compounds, dispersed in aqueous acetone mixtures. In the tests, seedling plants are grown in jiffy flats for about two weeks. The test compounds are dispersed in 50/50 acetone/water mixtures containing 0.5% TWEEN® 20, a polyoxyethylene sorbitan monolaurate surfactant of Atlas Chemical Industries, in sufficient quantities to provide the equivalent of about 0.16 kg to 8.0 kg per hectare of active compound when applied to the plants through a spray nozzle operating at 40 psig for a predetermined time. After spraying, the plants are placed on greenhouse benches and are cared for in the usual manner, commensurate with conventional greenhouse practices. From four to five weeks after treatment, the seedling plants are examined and rated according to the rating system provided in Example 11 above. The data obtained are recorded in Table II below. The compounds evaluated are reported by compound number given in Example 11.

TABLE II

POST-EMERGENCE TESTS - RATES IN KG/HA

| Compound No | RATE | BARNY ARDGR | FOXTAIL SP | P NUT SEDGE | WILD OATS | QUACK GRASS | FLD B INDWD | MRNGL RY SP | WILD MUSTD | VELVE TLEAF | WHT F ENMAN | SUGAR BEETS | CORN FIELD | COTTON | SOYBE AN WI |
|---|---|---|---|---|---|---|---|---|---|---|---|---|---|---|---|
| 1 | 1.000 | 2.7 | 0.0 | 3.7 | 1.7 | 2.0 | 3.7 | 2.7 | 9.0 | 3.0 | 2.0 | 8.0 | 4.0 | 4.0 | 2.3 |
|   | .500 | 1.7 | 1.0 | 4.0 | 1.0 | 1.0 | 1.7 | 1.0 | 7.0 | 1.7 | 1.0 | 8.0 | 1.0 | 3.3 | 2.3 |
|   | .250 | 0.7 | 0.0 | 2.7 | 0.3 | 0.3 | 0.7 | 0.7 | 5.0 | 1.0 | 0.5 | 6.7 | 1.0 | 2.0 | 1.7 |
|   | .125 | 0.0 | 0.0 | 1.3 | 0.3 | 0.0 | 0.7 | 0.7 | 8.0 | 0.3 | 0.5 | 6.3 | 1.0 | 1.0 | 1.3 |
| 2 | 1.000 | 0.0 |   | 0.0 | 0.0 | 0.0 | 0.0 | 0.0 | 0.0 | 0.0 |   | 0.0 | 0.0 | 0.0 | 1.0 |
|   | .500 | 0.0 |   | 0.0 | 0.0 | 0.0 | 0.0 | 0.0 | 0.0 | 0.0 |   | 0.0 | 1.0 | 0.0 | 1.0 |
|   | .250 | 0.0 |   | 0.0 | 0.0 | 0.0 | 0.0 | 0.0 | 0.0 | 0.0 |   | 0.0 | 0.0 | 0.0 | 1.0 |
|   | .125 | 0.0 |   | 0.0 | 0.0 | 0.0 | 0.0 | 0.0 | 0.0 | 0.0 |   | 0.0 | 0.0 | 0.0 | 1.0 |
| 3 | .500 | 9.0 | 8.0 | 7.0 | 9.0 | 7.0 | 7.0 | 7.0 | 9.0 | 7.0 | 9.0 | 9.0 | 7.0 | 7.0 | 6.0 |
|   | .250 | 9.0 | 9.0 | 7.0 | 8.0 | 7.0 | 7.0 | 7.0 | 7.0 | 8.0 | 9.0 | 9.0 | 7.0 | 7.0 | 6.0 |
|   | .125 | 9.0 | 9.0 | 2.0 | 8.0 | 5.0 | 3.0 | 7.0 | 5.0 | 5.0 | 7.0 | 9.0 | 5.0 | 3.0 | 4.0 |
| 4 | 1.000 | 9.0 | 9.0 | 6.0 | 8.0 | 8.0 | 7.0 | 7.0 | 8.0 | 8.0 | 9.0 | 9.0 | 7.0 | 8.0 | 7.0 |
|   | .500 | 9.0 | 8.0 | 5.0 | 8.0 | 7.0 | 7.0 | 7.0 | 0.0 | 8.0 | 8.0 | 9.0 | 7.0 | 8.0 | 7.0 |
|   | .250 | 8.0 | 8.0 | 5.0 | 8.0 | 7.0 | 7.0 | 7.0 | 0.0 | 7.0 | 8.0 | 8.8 | 6.0 | 7.0 | 7.0 |
| 5 | 1.000 | 2.0 | 2.0 | 1.0 | 3.0 | 3.0 | 3.0 | 0.0 |   | 3.0 | 0.0 | 9.0 | 0.0 | 0.0 | 3.0 |
|   | .500 | 1.0 | 1.0 | 0.0 | 2.0 | 2.0 | 2.0 | 0.0 |   | 2.0 | 0.0 | 5.0 | 0.0 | 0.0 | 3.0 |
|   | .250 | 0.0 | 0.0 | 1.0 | 0.0 | 1.0 | 1.0 | 0.0 |   | 1.0 | 0.0 | 0.0 | 0.0 | 0.0 | 2.0 |
|   | .125 | 0.0 | 0.0 | 0.0 | 0.0 | 0.0 | 1.0 | 0.0 |   | 0.0 | 0.0 | 0.0 | 4.0 | 0.0 | 3.0 |
| 6 | .500 | 0.0 | 0.0 | 3.0 | 1.0 | 0.0 | 2.0 | 0.0 |   | 4.0 | 0.0 | 0.0 | 3.0 | 5.0 | 2.0 |
|   | .250 | 0.0 | 0.0 | 2.0 | 0.0 | 0.0 | 2.0 | 0.0 |   | 0.0 | 4.0 | 8.0 | 3.0 | 4.0 | 2.0 |
|   | .125 | 0.0 | 0.0 | 0.0 | 0.0 | 0.0 | 2.0 | 0.0 |   | 0.0 | 1.0 | 8.0 | 6.0 | 4.0 | 2.0 |
| 7 | 1.000 | 4.0 | 3.0 | 4.0 | 7.0 | 0.0 | 4.0 | 7.0 |   | 9.0 | 1.0 | 8.0 | 3.0 | 9.0 | 8.0 |
|   | .500 | 3.0 | 2.0 | 2.0 | 5.0 | 0.0 | 4.0 | 6.0 |   | 9.0 | 0.0 | 8.0 | 6.0 | 7.0 | 7.0 |
|   | .250 | 2.0 | 0.0 | 0.0 | 4.0 | 0.0 | 0.0 | 5.0 |   | 7.0 | 0.0 | 9.0 | 5.0 | 9.0 | 7.0 |
|   | .125 | 0.0 | 0.0 | 0.0 | 1.0 | 0.0 | 0.0 | 4.0 |   | 5.0 | 0.0 | 9.0 | 4.0 | 7.0 | 6.0 |
| 8 | 1.000 | 9.0 | 9.0 | 9.0 | 9.0 | 8.0 | 9.0 | 9.0 |   | 9.0 | 9.0 | 6.0 | 9.0 | 6.0 | 9.0 |
|   | .500 | 9.0 | 9.0 | 7.0 | 9.0 | 8.0 | 8.0 | 9.0 |   | 9.0 | 9.0 | 5.0 | 5.0 | 9.0 | 9.0 |
|   | .250 | 9.0 | 9.0 | 7.0 | 9.0 | 7.0 | 9.0 | 9.0 |   | 9.0 | 9.0 | 0.0 | 4.0 | 9.0 | 9.0 |
|   | .125 | 7.0 | 9.0 | 8.5 | 9.0 | 8.0 | 9.0 | 9.0 | 9.0 | 9.0 | 8.5 | 5.0 | 9.0 | 9.0 | 8.0 |
| 9 | 1.000 | 9.0 | 8.5 | 7.5 | 9.0 | 7.0 | 8.0 | 8.5 | 9.0 | 9.0 | 8.0 | 9.0 | 9.0 | 9.0 | 9.0 |
|   | .500 | 9.0 | 8.5 | 7.0 | 9.0 | 5.0 | 8.0 | 8.5 | 9.0 | 9.0 | 5.5 | 9.0 | 8.5 | 9.0 | 8.0 |
|   | .250 | 8.0 | 8.5 | 4.5 | 9.0 | 4.0 | 8.5 | 8.0 | 9.0 | 9.0 | 2.5 | 9.0 | 2.5 | 8.5 | 7.5 |
|   | .125 | 8.0 | 7.5 | 0.0 | 9.0 | 3.0 | 0.0 | 0.0 | 8.0 | 8.0 | 0.0 | 9.0 | 0.0 | 8.0 | 8.0 |
| 10 | 1.000 | 0.0 | 0.0 | 0.0 | 0.0 | 0.0 | 0.0 | 0.0 | 9.0 | 0.0 | 0.0 | 6.0 | 0.0 | 0.0 | 0.0 |
|   | .500 | 0.0 | 0.0 | 0.0 | 0.0 | 0.0 | 0.0 | 0.0 | 9.0 | 0.0 | 0.0 | 4.0 | 0.0 | 0.0 | 0.0 |
|   | .250 | 0.0 | 0.0 | 0.0 | 0.0 | 0.0 | 0.0 | 0.0 | 8.0 | 0.0 | 0.0 | 2.0 | 0.0 | 0.0 | 0.0 |
|   | .125 | 0.0 | 0.0 | 0.0 | 0.0 | 0.0 | 0.0 | 0.0 | 9.0 | 0.0 | 0.0 | 0.0 | 0.0 | 0.0 | 0.0 |
| 11 | 1.000 | 2.0 | 0.0 | 2.0 | 4.0 | 2.0 | 3.0 | 5.0 | 9.0 | 3.0 |   | 7.0 | 4.0 | 0.0 | 5.0 |
|   | .500 | 0.0 | 0.0 | 1.0 | 2.0 | 0.0 | 2.0 | 5.0 | 8.0 | 3.0 |   | 6.0 | 4.0 | 6.0 | 4.0 |
|   | .250 | 0.0 | 0.0 | 0.0 | 0.0 | 0.0 | 0.0 | 1.0 | 4.0 | 1.0 |   | 0.0 | 3.0 | 6.0 | 3.0 |
|   | .125 | 0.0 | 0.0 | 0.0 | 0.0 | 0.0 | 0.0 | 0.0 | 3.0 | 0.0 |   | 0.0 | 3.0 | 5.0 | 1.0 |
| 12 | 1.000 | 9.0 | 9.0 | 8.0 | 9.0 | 8.0 | 9.0 | 9.0 | 9.0 | 8.0 | 9.0 | 9.0 | 9.0 | 9.0 | 9.0 |
|   | .500 | 7.0 | 9.0 | 7.0 | 9.0 | 8.0 | 9.0 | 8.0 | 9.0 | 9.0 | 9.0 | 9.0 | 8.0 | 9.0 | 9.0 |
|   | .250 | 7.0 | 8.0 | 4.0 | 9.0 | 7.0 | 7.0 | 8.0 | 9.0 | 7.0 | 8.0 | 9.0 | 7.0 | 9.0 | 9.0 |
| 13 | 1.000 | 5.0 | 7.0 | 9.0 | 9.0 | 2.0 | 9.0 | 8.0 | 8.0 | 9.0 | 8.0 | 9.0 | 9.0 | 9.0 | 8.0 |
|   | .500 | 9.0 | 9.0 | 8.0 | 9.0 | 0.0 | 9.0 | 7.0 | 8.0 | 8.0 | 2.0 | 9.0 | 7.0 | 9.0 | 8.0 |
|   | .250 | 8.0 | 6.0 | 4.0 | 8.0 | 0.0 | 7.0 | 7.0 | 8.0 | 8.0 | 1.0 | 9.0 | 4.0 | 8.0 | 7.0 |
|   | .125 | 4.0 | 4.0 | 2.0 | 8.0 | 0.0 | 7.0 | 7.0 | 8.0 | 7.0 | 1.0 | 9.0 | 2.0 | 8.0 | 6.0 |
| 14 | 1.000 | 8.0 | 8.0 | 0.0 | 4.0 | 4.0 | 7.0 | 4.0 | 8.0 | 7.0 | 2.0 | 9.0 | 2.0 | 6.0 | 0.0 |

TABLE II-continued

POST-EMERGENCE TESTS - RATES IN KG/HA

| Compound No | RATE | BARNY ARDGR | FOXTA IL SP | P NUT SEDGE | WILD OATS | QUACK GRASS | FLD B INDWD | MRNGL RY SP | WILD MUSTD | VELVE TLEAF | WHT F ENMAN | SUGAR BEETS | CORN FIELD | COTTON | SOYBE AN WI |
|---|---|---|---|---|---|---|---|---|---|---|---|---|---|---|---|
| 15 | .500 | 6.0 | 7.0 | 0.0 | 4.0 | 2.0 | 7.0 | 4.0 | 7.0 | 8.0 | 1.0 | 9.0 | 1.0 | 6.0 | 0.0 |
|  | .250 | 2.0 | 4.0 | 0.0 | 2.0 | 2.0 | 7.0 | 4.0 | 7.0 | 7.0 | 0.0 | 9.0 | 0.0 | 6.0 | 0.0 |
|  | .125 | 2.0 | 2.0 | 0.0 | 2.0 | 0.0 | 7.0 | 2.0 | 7.0 | 7.0 | 0.0 | 9.0 | 0.0 | 6.0 | 0.0 |
| 16 | 1.000 | 9.0 | 9.0 | 9.0 | 9.0 | 8.0 | 9.0 | 9.0 | 9.0 | 9.0 | 9.0 | 9.0 | 9.0 | 8.0 | 9.0 |
|  | .500 | 9.0 | 9.0 | 9.0 | 9.0 | 8.0 | 9.0 | 8.0 | 9.0 | 9.0 | 9.0 | 9.0 | 9.0 | 7.0 | 3.0 |
|  | .250 | 8.0 | 7.0 | 8.0 | 7.0 | 8.0 | 9.0 | 7.0 | 9.0 | 9.0 | 6.0 | 9.0 | 9.0 | 7.0 | 1.0 |
|  | .125 | 9.0 | 9.0 | 9.0 | 4.0 | 8.0 | 9.0 | 9.0 | 9.0 | 9.0 | 2.0 | 9.0 | 9.0 | 7.0 | 0.0 |
| 17 | 1.000 | 9.0 | 9.0 | 9.0 | 9.0 | 9.0 | 9.0 | 9.0 | 9.0 | 9.0 | 9.0 | 9.0 | 9.0 | 8.0 | 0.0 |
|  | .500 | 9.0 | 9.0 | 8.0 | 8.0 | 8.0 | 9.0 | 9.0 | 9.0 | 9.0 | 9.0 | 9.0 | 9.0 | 8.0 | 0.0 |
|  | .250 | 9.0 | 9.0 | 7.0 | 3.0 | 7.0 | 9.0 | 7.0 | 9.0 | 9.0 | 4.0 | 9.0 | 4.0 | 7.0 | 0.0 |
|  | .125 | 9.0 | 4.0 | 4.0 | 2.0 | 4.0 | 7.0 | 4.0 | 8.0 | 6.0 | 2.0 | 9.0 | 7.0 | 4.0 | 0.0 |
| 19 | 1.000 | 8.0 | 4.0 | 4.0 | 1.0 | 4.0 | 8.0 | 4.0 | 9.0 | 8.0 | 1.0 | 9.0 | 6.0 | 2.0 | 0.0 |
|  | .500 | 2.0 | 2.0 | 2.0 | 1.0 | 4.0 | 6.0 | 4.0 | 7.0 | 7.0 | 0.0 | 8.0 | 5.0 | 2.0 | 0.0 |
|  | .250 | 9.0 | 8.0 | 2.0 | 8.0 | 0.0 | 4.0 | 4.0 | 9.0 | 2.0 | 0.0 | 7.0 | 3.0 | 1.0 | 0.0 |
|  | .125 | 9.0 | 9.0 | 7.0 | 9.0 | 8.0 | 4.0 | 7.0 | 9.0 | 7.0 | 7.0 | 9.0 | 9.0 | 8.0 | 0.0 |
| 20 | 1.000 | 9.0 | 8.0 | 7.0 | 8.0 | 9.0 | 4.0 | 8.0 | 9.0 | 7.0 | 6.0 | 9.0 | 9.0 | 8.0 | 0.0 |
|  | .500 | 8.0 | 7.0 | 5.0 | 8.0 | 7.0 | 4.0 | 7.0 | 9.0 | 7.0 | 1.0 | 9.0 | 9.0 | 7.0 | 0.0 |
|  | .250 | 9.0 | 9.0 | 3.0 | 4.0 | 3.0 | 2.0 | 4.0 | 9.0 | 8.0 | 9.0 | 9.0 | 9.0 | 9.0 | 6.0 |
|  | .125 | 9.0 | 9.0 | 9.0 | 9.0 | 9.0 | 9.0 | 9.0 | 9.0 | 4.0 | 9.0 | 9.0 | 9.0 | 9.0 | 6.0 |
| 21 | 1.000 | 9.0 | 9.0 | 9.0 | 8.0 | 9.0 | 9.0 | 9.0 | 9.0 | 9.0 | 9.0 | 8.0 | 9.0 | 9.0 | 5.0 |
|  | .500 | 9.0 | 9.0 | 9.0 | 8.0 | 7.0 | 9.0 | 9.0 | 9.0 | 7.0 | 9.0 | 9.0 | 9.0 | 8.0 | 4.0 |
|  | .250 | 8.0 | 9.0 | 9.0 | 4.0 | 8.0 | 9.0 | 8.0 | 9.0 | 6.5 | 7.0 | 7.0 | 9.0 | 6.0 | 1.0 |
|  | .125 | 8.0 | 9.0 | 9.0 | 9.0 | 9.0 | 9.0 | 9.0 | 9.0 | 9.0 | 9.0 | 9.0 | 9.0 | 8.0 | 9.0 |
| 22 | 1.000 | 9.0 | 9.0 | 9.0 | 9.0 |  | 9.0 | 9.0 | 9.0 | 9.0 | 9.0 | 9.0 | 9.0 | 9.0 | 8.0 |
|  | .500 | 2.0 | 9.0 | 8.0 | 9.0 | 9.0 | 9.0 | 9.0 | 9.0 | 9.0 | 8.0 | 9.0 | 7.0 | 9.0 | 8.0 |
|  | .250 | 0.0 | 9.0 | 7.0 | 9.0 | 6.0 | 9.0 | 9.0 | 9.0 | 9.0 | 6.0 | 9.0 | 9.0 | 9.0 | 6.0 |
|  | .125 | 0.0 | 9.0 | 8.0 | 9.0 | 6.0 | 9.0 | 6.0 | 8.0 | 8.0 | 9.0 | 9.0 | 8.0 | 8.0 | 8.0 |
| 23 | 1.000 | 9.0 | 9.0 | 7.0 | 9.0 | 6.0 | 9.0 | 6.0 | 9.0 | 9.0 | 2.0 | 9.0 | 8.0 | 8.0 | 6.0 |
|  | .500 | 9.0 | 9.0 | 8.0 | 9.0 | 6.0 | 9.0 | 5.0 | 9.0 | 9.0 | 3.0 | 9.0 | 9.0 | 9.0 | 5.0 |
|  | .250 | 9.0 | 9.0 | 7.0 | 9.0 | 8.0 | 9.0 | 7.0 | 9.0 | 9.0 | 9.0 | 9.0 | 9.0 | 9.0 | 9.0 |
|  | .125 | 8.0 | 9.0 | 4.0 | 9.0 | 6.0 | 9.0 | 7.0 | 9.0 | 9.0 | 3.0 | 9.0 | 8.0 | 9.0 | 9.0 |
| 24 | 1.000 | 8.0 | 9.0 | 0.0 | 9.0 | 4.0 | 9.0 | 6.0 | 9.0 | 9.0 | 9.0 | 9.0 | 9.0 | 9.0 | 9.0 |
|  | .500 | 2.0 | 9.0 | 0.0 | 9.0 | 6.0 | 9.0 | 5.0 | 9.0 | 9.0 | 3.0 | 9.0 | 8.0 | 9.0 | 8.0 |
|  | .250 | 0.0 | 9.0 | 0.0 | 2.0 | 4.0 | 9.0 | 5.0 | 9.0 | 9.0 | 8.0 | 9.0 | 8.0 | 9.0 | 6.0 |
|  | .125 | 0.0 | 9.0 | 0.0 | 7.0 | 4.0 | 9.0 | 8.0 | 9.0 | 9.0 | 6.0 | 9.0 | 8.0 | 7.0 | 6.0 |
| 25 | 1.000 | 2.0 | 7.0 | 0.0 | 4.0 | 0.0 | 9.0 | 7.0 | 9.0 | 9.0 | 3.0 | 9.0 | 7.0 | 6.0 | 6.0 |
|  | .500 | 0.0 | 9.0 | 0.0 | 2.0 | 4.0 | 4.0 | 8.0 | 9.0 | 4.0 | 5.0 | 9.0 | 3.0 | 7.0 | 3.0 |
|  | .250 | 0.0 | 8.0 | 7.0 | 8.0 | 2.0 | 4.0 | 6.0 | 9.0 | 0.0 | 3.0 | 8.0 | 9.0 | 8.0 | 0.0 |
|  | .125 | 7.0 | 7.0 | 6.0 | 9.0 | 0.0 | 7.0 | 6.0 | 8.0 | 6.0 | 0.0 | 1.0 | 9.0 | 9.0 | 0.0 |
| 26 | 1.000 | 7.0 | 4.0 | 6.0 | 9.0 | 0.0 | 2.0 | 4.0 | 1.0 | 0.0 | 0.0 | 0.0 | 2.0 | 0.0 | 7.0 |
|  | .500 | 4.0 | 2.0 | 2.0 | 8.0 | 0.0 | 0.0 | 0.0 | 9.0 | 6.0 | 0.0 | 0.0 | 0.0 | 0.0 | 4.0 |
|  | .250 | 0.0 | 0.0 | 0.0 | 0.0 | 0.0 | 7.0 | 0.0 | 9.0 | 0.0 | 0.0 | 0.0 | 0.0 | 0.0 | 0.0 |
|  | .125 | 0.0 | 0.0 | 0.0 | 0.0 | 8.0 | 2.0 | 0.0 | 9.0 | 0.0 | 9.0 | 9.0 | 9.0 | 9.0 | 8.0 |
| 27 | .500 | 8.0 | 9.0 | 9.0 | 0.0 | 8.0 | 9.0 | 0.0 | 9.0 | 9.0 | 9.0 | 0.0 | 9.0 | 9.0 | 9.0 |
|  | .250 | 8.0 | 9.0 | 8.0 | 0.0 | 8.0 | 9.0 | 0.0 | 9.0 | 9.0 | 9.0 | 0.0 | 9.0 | 9.0 | 8.0 |
|  | .125 | 6.0 | 9.0 | 7.0 | 0.0 | 9.0 | 9.0 | 0.0 | 9.0 | 9.0 | 9.0 | 9.0 | 9.0 | 8.0 | 7.0 |

TABLE II-continued

POST-EMERGENCE TESTS - RATES IN KG/HA

| Compound No | RATE | BARNY ARDGR | FOXTAIL SP | P NUT SEDGE | WILD OATS | QUACK GRASS | FLD B INDWD | MRNGL RY SP | WILD MUSTD | VELVE TLEAF | WHT F ENMAN | SUGAR BEETS | CORN FIELD | COTTON | SOYBE AN WI |
|---|---|---|---|---|---|---|---|---|---|---|---|---|---|---|---|
| 28 | 1.000 | 9.0 | 9.0 | 9.0 | 9.0 | 9.0 | 9.0 | 8.0 | 9.0 | 9.0 | 8.0 | 9.0 | 9.0 | 9.0 | 9.0 |
|    | .500  | 9.0 | 8.0 | 8.0 | 9.0 | 9.0 | 9.0 | 8.0 | 9.0 | 9.0 | 9.0 | 9.0 | 9.0 | 9.0 | 9.0 |
|    | .250  | 8.0 | 8.0 | 8.0 | 9.0 | 9.0 | 8.0 | 7.0 | 8.0 | 9.0 | 6.0 | 9.0 | 9.0 | 8.0 | 8.0 |
|    | .125  | 7.0 | 7.0 | 6.0 | 9.0 | 9.0 | 8.0 | 6.0 | 8.0 | 9.0 | 5.0 | 9.0 | 4.0 | 7.0 | 7.0 |
| 29 | 1.000 | 9.0 | 9.0 | 9.0 | 9.0 | 9.0 | 9.0 | 9.0 | 9.0 | 9.0 | 9.0 | 9.0 | 9.0 | 9.0 | 8.0 |
|    | .500  | 8.0 | 9.0 | 7.0 | 9.0 | 9.0 | 8.0 | 9.0 | 9.0 | 9.0 | 9.0 | 9.0 | 9.0 | 9.0 | 8.0 |
|    | .250  | 8.0 | 9.0 | 7.0 | 9.0 | 9.0 | 8.0 | 9.0 | 9.0 | 8.0 | 9.0 | 9.0 | 9.0 | 8.0 | 8.0 |
|    | .125  | 2.0 | 9.0 | 7.0 | 8.0 | 9.0 | 8.0 | 9.0 | 9.0 | 8.0 | 8.0 | 9.0 | 9.0 | 8.0 | 7.0 |
| 30 | 1.000 | 9.0 | 9.0 | 9.0 | 9.0 | 9.0 | 9.0 | 9.0 | 9.0 | 9.0 | 9.0 | 9.0 | 9.0 | 8.0 | 8.0 |
|    | .500  | 8.0 | 9.0 | 7.0 | 8.0 | 8.0 | 9.0 | 6.0 | 9.0 | 9.0 | 7.0 | 9.0 | 9.0 | 8.0 | 6.0 |
|    | .250  | 9.0 | 9.0 | 7.0 | 6.0 | 6.0 | 9.0 | 7.0 | 9.0 | 9.0 | 5.0 | 9.0 | 9.0 | 8.0 | 6.0 |
|    | .125  | 9.0 | 9.0 | 7.0 | 7.0 | 2.0 | 9.0 | 9.0 | 9.0 | 9.0 | 4.0 | 9.0 | 3.0 | 7.0 | 7.0 |
| 31 | 1.000 | 9.0 | 9.0 | 8.0 | 9.0 | 9.0 | 9.0 | 8.0 | 9.0 | 9.0 | 9.0 | 9.0 | 9.0 | 9.0 | 4.0 |
|    | .500  | 9.0 | 9.0 | 7.0 | 9.0 | 9.0 | 8.0 | 9.0 | 9.0 | 9.0 | 9.0 | 9.0 | 9.0 | 9.0 | 7.0 |
|    | .250  | 8.0 | 9.0 | 6.0 | 9.0 | 9.0 | 7.0 | 9.0 | 9.0 | 9.0 | 9.0 | 9.0 | 9.0 | 9.0 | 8.0 |
|    | .125  | 9.0 | 9.0 | 2.0 | 8.0 | 4.0 | 8.0 | 9.0 | 9.0 | 8.0 | 2.0 | 9.0 | 9.0 | 9.0 | 6.0 |
| 32 | 1.000 | 9.0 | 9.0 | 7.0 | 9.0 | 0.0 | 9.0 | 7.0 | 9.0 | 9.0 | 1.0 | 9.0 | 2.0 | 9.0 | 6.0 |
|    | .500  | 9.0 | 9.0 | 9.0 | 9.0 | 0.0 | 9.0 | 6.0 | 9.0 | 9.0 | 3.0 | 9.0 | 3.0 | 7.0 | 4.0 |
|    | .250  | 9.0 | 9.0 | 7.0 | 9.0 | 0.0 | 9.0 | 2.0 | 9.0 | 9.0 | 1.0 | 9.0 | 4.0 | 7.0 | 4.0 |
|    | .125  | 9.0 | 9.0 | 7.0 | 9.0 | 0.0 | 9.0 | 8.0 | 9.0 | 9.0 | 9.0 | 9.0 | 2.0 | 7.0 | 4.0 |
| 33 | 1.000 | 9.0 | 9.0 | 4.0 | 9.0 | 9.0 | 9.0 | 7.0 | 9.0 | 9.0 | 9.0 | 9.0 | 9.0 | 9.0 | 6.0 |
|    | .500  | 9.0 | 9.0 | 9.0 | 9.0 | 9.0 | 9.0 | 8.0 | 9.0 | 9.0 | 9.0 | 9.0 | 9.0 | 8.0 | 4.0 |
|    | .250  | 9.0 | 9.0 | 8.0 | 9.0 | 9.0 | 9.0 | 8.0 |     | 9.0 | 8.0 | 9.0 | 9.0 | 8.0 | 2.0 |
|    | .125  | 8.0 | 8.0 | 7.0 | 9.0 | 9.0 | 9.0 | 7.0 |     | 9.0 | 9.0 | 9.0 | 9.0 | 9.0 | 1.0 |
| 34 | 1.000 | 9.0 | 9.0 | 9.0 | 9.0 | 4.0 | 9.0 | 9.0 |     | 9.0 | 9.0 | 9.0 | 9.0 | 9.0 | 9.0 |
|    | .500  | 9.0 | 9.0 | 8.0 | 9.0 | 4.0 | 9.0 | 8.0 |     | 9.0 | 6.0 | 9.0 | 9.0 | 8.0 | 9.0 |
|    | .250  | 7.0 | 9.0 | 8.0 | 9.0 | 1.0 | 9.0 | 7.0 |     | 9.0 | 4.0 | 9.0 | 9.0 | 8.0 | 9.0 |
|    | .125  | 9.0 | 8.0 | 6.0 | 9.0 | 0.0 | 9.0 | 7.0 |     | 9.0 | 1.0 | 9.0 | 9.0 | 8.0 | 8.0 |
| 35 | 1.000 | 9.0 | 9.0 | 8.0 | 9.0 | 4.0 | 9.0 | 9.0 |     | 9.0 | 9.0 | 9.0 | 9.0 | 8.0 | 8.0 |
|    | .500  | 8.0 | 9.0 | 8.0 | 9.0 | 1.0 | 9.0 | 7.0 |     | 9.0 | 4.0 | 9.0 | 9.0 | 8.0 | 8.0 |
|    | .250  | 7.0 | 8.0 | 6.0 | 9.0 | 0.0 | 9.0 | 7.0 |     | 8.0 | 1.0 | 9.0 | 6.0 | 8.0 | 7.0 |
|    | .125  | 9.0 | 7.0 | 8.0 | 9.0 | 6.0 | 7.0 | 6.0 |     | 8.0 | 7.0 | 9.0 | 2.0 | 7.0 | 7.0 |
| 36 | 1.000 | 8.0 | 9.0 | 6.0 | 9.0 | 3.0 | 9.0 | 4.0 |     | 9.0 | 4.0 | 9.0 | 2.0 | 7.0 | 6.0 |
|    | .500  | 7.0 | 9.0 | 4.0 | 9.0 | 7.0 | 8.0 | 5.0 |     | 7.0 | 2.0 | 9.0 | 2.0 | 7.0 | 7.0 |
|    | .250  | 2.0 | 7.0 | 6.0 | 9.0 | 4.0 | 7.0 | 4.0 |     | 7.0 | 1.0 | 9.0 | 2.0 | 7.0 | 4.0 |

What is claimed is:

1. A compound having the formula I structure:

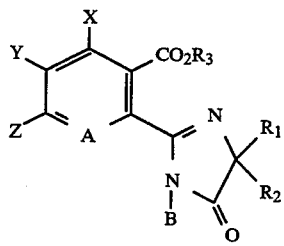

wherein

X is hydrogen, halogen or methyl;

Y and Z are each hydrogen, halogen,
$C_1$–$C_6$ alkyl optionally substituted with $C_1$–$C_3$ alkoxy;
$C_1$–$C_3$ alkoxy, phenoxy, $C_1$–$C_3$ haloalkyl, trifluoromethoxy, $C_1$–$C_4$ hydroxyalkyl, $C_1$–$C_4$ alkylthio, formyl, difluoromethoxy, 1,1,2,2-tetrafluoroethoxy, nitro, cyano, $C_1$–$C_4$ alkylsulfonyl, $C_2$–$C_6$ alkenyl optionally substituted with halogen;
$C_2$–$C_6$ alkynyl optionally substituted with halogen;
or phenyl optionally substituted with $C_1$–$C_3$ alkyl, $C_1$–$C_3$ alkoxy, or halogen;

and, when taken together, Y and Z may form a ring in which YZ are represented by the structure: —$(CH_2)_n$—, where n is an integer of 3 or 4; or

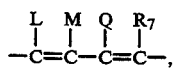

where L, M, Q and $R_7$ are each hydrogen, halogen, $C_1$–$C_4$ alkyl, $C_1$–$C_4$ alkoxy, $C_1$–$C_4$ alkylsulfonyl, $C_1$–$C_4$ haloalkyl, difluoromethoxy, trifluoromethoxy, 1,1,2,2-tetrafluoroethoxy, nitro, cyano, phenyl optionally substituted with halogen or $C_1$–$C_3$ alkyl;
phenoxy optionally substituted with halogen, trifluoromethyl, nitro or $C_1$–$C_3$ alkyl; $C_3$–$C_6$ alkenyl optionally substituted with halogen; or $C_3$–$C_6$ alkynyl optionally substituted with halogen;

A is $CR_6$;

B is hydroxyl, cyano, halogen, $SR_4$,

$R_1$ is $C_1$–$C_4$ alkyl;

$R_2$ is $C_1$–$C_4$ alkyl or $C_3$–$C_6$ cycloalkyl;

and when $R_1$ and $R_2$ are taken together with the carbon to which they are attached they may represent $C_3$–$C_6$ cycloalkyl optionally substituted with methyl;

$R_3$ is hydrogen,
$C_1$–$C_6$ alkyl optionally substituted with $C_1$–$C_3$ alkoxy, halogen, $C_3$–$C_6$ cycloalkyl, benzyl, furyl, trimethylsilyl, phenyl, halophenyl, $C_1$–$C_4$ alkylphenyl, $C_1$–$C_4$ alkoxyphenyl, or nitrophenyl;
$C_3$–$C_6$ alkenyl optionally substituted with $C_1$–$C_3$ alkoxy, phenyl, halogen or $C_1$–$C_4$ alkoxycarbonyl;
$C_3$–$C_6$ cycloalkyl optionally substituted with $C_1$–$C_3$ alkyl;
$C_3$–$C_6$ alkynyl optionally substituted with $C_1$–$C_3$ alkyl; or
a cation of alkali metals, ammonium or organic ammonium;

$R_4$ is $C_1$–$C_4$ alkyl, or phenyl optionally substituted with nitro, $CO_2R_8$, cyano, trifluoromethyl, difluoromethyl, $C_1$–$C_4$ alkyl, $C_1$–$C_4$ alkoxy, or halogen;

$R_5$ is $C_1$–$C_4$ alkyl;

$R_6$ is hydrogen, halogen, $C_1$–$C_4$ alkyl, $C_1$–$C_4$ alkoxy, trifluoromethyl, trifluoromethoxy, difluoromethoxy or 1,1,2-2-tetrafluoroethoxy;

$R_8$ is hydrogen or $C_1$–$C_4$ alkyl;

the N-oxides thereof, when $R_3$ is not unsaturated alkyl and Y and Z cannot be unsaturated alkyl or alkylthio;

the optical isomers thereof, when $R_1$ and $R_2$ represent different substituents; and the acid addition salts thereof, when $R_3$ is other than a cation.

2. A method for controlling undesirable plant species which comprises applying to the foliage of said plants or to the soil or water containing seeds or other propagating organs thereof, a herbicidally effective amount of a compound having the structure:

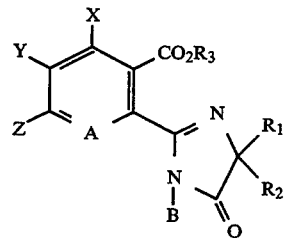

wherein

X is hydrogen, halogen or methyl;

Y and Z are each hydrogen, halogen,
$C_1$–$C_6$ alkyl optionally substituted with $C_1$–$C_3$ alkoxy;
$C_1$–$C_3$ alkoxy, phenoxy, $C_1$–$C_3$ haloalkyl, trifluoromethoxy, $C_1$–$C_4$ hydroxyalkyl, $C_1$–$C_4$ alkylthio, formyl, difluoromethoxy, 1,1,2,2-tetrafluoroethoxy, nitro, cyano, $C_1$–$C_4$ alkylsulfonyl, $C_2$–$C_6$ alkenyl optionally substituted with halogen;
$C_2$–$C_6$ alkynyl optionally substituted with halogen;
or phenyl optionally substituted with $C_1$–$C_3$ alkyl, $C_1$–$C_3$ alkoxy, or halogen;

and, when taken together, Y and Z may form a ring in which YZ are represented by the structure: —$(CH_2)_n$—, where n is an integer of 3 or 4; or

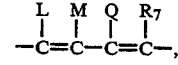

where L, M, Q and $R_7$ are each hydrogen, halogen, $C_1$–$C_4$ alkyl, $C_1$–$C_4$ alkoxy, $C_1$–$C_4$ alkylsulfonyl, $C_1$–$C_4$ haloalkyl, difluoromethoxy, trifluoromethoxy, 1,1,2,2-tetrafluoroethoxy, nitro, cyano, phenyl optionally substituted with halogen or $C_1$–$C_3$ alkyl;
phenoxy optionally substituted with halogen, trifluoromethyl, nitro or $C_1$–$C_3$ alkyl; $C_3$–$C_6$ alkenyl optionally substituted with halogen; or $C_3$–$C_6$ alkynyl optionally substituted with halogen;

A is $CR_6$;

B is hydroxyl, cyano, halogen, $SR_4$,

or $P(OR_5)_2$;

$R_1$ is $C_1$–$C_4$ alkyl;

$R_2$ is $C_1$–$C_4$ alkyl or $C_3$–$C_6$ cycloalkyl;

and when $R_1$ and $R_2$ are taken together with the carbon to which they are attached they may represent $C_3$–$C_6$ cycloalkyl optionally substituted with methyl;

$R_3$ is hydrogen, $C_1$–$C_6$ alkyl optionally substituted with $C_1$–$C_3$ alkoxy, halogen, $C_3$–$C_6$ cycloalkyl, benzyl, furyl, trimethylsilyl, phenyl, halophenyl, $C_1$–$C_4$ alkylphenyl, $C_1$–$C_4$ alkoxyphenyl, or nitrophenyl;

$C_3$–$C_6$ alkenyl optionally substituted with $C_1$–$C_3$ alkoxy, phenyl, halogen or $C_1$–$C_4$ alkoxycarbonyl;

$C_3$–$C_6$ cycloalkyl optionally substituted with $C_1$–$C_3$ alkyl;

$C_3$–$C_6$ alkynyl optionally substituted with $C_1$–$C_3$ alkyl; or a cation of alkali metals, ammonium or organic ammonium;

$R_4$ is $C_1$–$C_4$ alkyl, or phenyl optionally substituted with nitro, $CO_2R_8$, cyano, trifluoromethyl, difluoromethyl, $C_1$–$C_4$ alkyl, $C_1$–$C_4$ alkoxy, or halogen;

$R_5$ is $C_1$–$C_4$ alkyl;

$R_6$ is hydrogen, halogen, $C_1$–$C_4$ alkyl, $C_1$–$C_4$ alkoxy, trifluoromethyl, trifluoromethoxy, difluoromethoxy or 1,1,2-2-tetrafluoroethoxy;

$R_8$ is hydrogen or $C_1$–$C_4$ alkyl;

the N-oxides thereof, when $R_3$ is not unsaturated alkyl and Y and Z cannot be unsaturated alkyl or alkylthio;

the optical isomers thereof, when $R_1$ and $R_2$ represent different substituents; and the acid addition salts thereof, when $R_3$ is other than a cation.

3. The method according to claim 2, which comprises applying said compound to the foliage of said plants at a rate of about 0.016 kg/ha to 4.0 kg/ha.

4. The method according to claim 2, which comprises applying said compound to the soil or water containing seeds or other propagating organs of said plants at a rate of about 0.016 kg/ha to 4.0 kg/ha.

5. A composition for controlling undesirable plant species which comprises an agronomically acceptable carrier and a herbicidally effective amount of a 2-(1-substituted-2-imidazolin-2-yl)benzoic or nicotinic acid, ester or salt compound as described in claim 1.

* * * * *